US011752086B2

(12) United States Patent
Peters

(10) Patent No.: US 11,752,086 B2
(45) Date of Patent: Sep. 12, 2023

(54) TOPICAL FORMULATIONS AND METHODS

(71) Applicant: MYOCEPT INC., Novato, CA (US)

(72) Inventor: Lars Erik Peters, Falmouth, ME (US)

(73) Assignee: MYOCEPT INC., Novato, CA (US)

(*) Notice: Subject to any disclaimer, the term of this patent is extended or adjusted under 35 U.S.C. 154(b) by 0 days.

(21) Appl. No.: 16/484,430

(22) PCT Filed: Feb. 7, 2018

(86) PCT No.: PCT/US2018/017301
§ 371 (c)(1),
(2) Date: Aug. 7, 2019

(87) PCT Pub. No.: WO2018/148338
PCT Pub. Date: Aug. 16, 2018

(65) Prior Publication Data

US 2020/0009040 A1 Jan. 9, 2020

Related U.S. Application Data

(60) Provisional application No. 62/456,066, filed on Feb. 7, 2017.

(51) Int. Cl.

| | |
|---|---|
| ***A61K 8/81*** | (2006.01) |
| ***A61K 8/06*** | (2006.01) |
| ***A61K 8/64*** | (2006.01) |
| ***A61K 8/73*** | (2006.01) |
| ***A61K 9/00*** | (2006.01) |
| ***A61K 9/107*** | (2006.01) |
| ***A61K 31/728*** | (2006.01) |
| ***A61K 38/08*** | (2019.01) |
| ***A61K 38/17*** | (2006.01) |
| ***A61K 38/28*** | (2006.01) |
| ***A61K 45/06*** | (2006.01) |
| ***A61K 47/32*** | (2006.01) |
| ***A61K 47/58*** | (2017.01) |
| ***A61P 17/00*** | (2006.01) |
| ***A61P 17/18*** | (2006.01) |
| ***A61Q 19/00*** | (2006.01) |
| ***A61Q 19/08*** | (2006.01) |

(52) U.S. Cl.
CPC ............ *A61K 8/8158* (2013.01); *A61K 8/068* (2013.01); *A61K 8/64* (2013.01); *A61K 8/735* (2013.01); *A61K 9/0014* (2013.01); *A61K 9/1075* (2013.01); *A61K 31/728* (2013.01); *A61K 38/08* (2013.01); *A61K 38/1703* (2013.01); *A61K 38/1709* (2013.01); *A61K 38/28* (2013.01); *A61K 45/06* (2013.01); *A61K 47/32* (2013.01); *A61K 47/58* (2017.08); *A61P 17/00* (2018.01); *A61P 17/18* (2018.01); *A61Q 19/00* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 2008/0305989 A1* | 12/2008 | Wen | A61K 9/0014 514/1.1 |
| 2009/0322327 A1 | 12/2009 | Gao et al. | |
| 2010/0150994 A1* | 6/2010 | Kotyla | A61K 9/1075 424/449 |
| 2011/0117026 A1* | 5/2011 | Tseng | C07C 279/10 424/9.6 |
| 2011/0118190 A1 | 5/2011 | Peters et al. | |
| 2012/0189677 A1* | 7/2012 | Tonge | A61K 8/64 424/401 |
| 2016/0199498 A1 | 7/2016 | Dai et al. | |

FOREIGN PATENT DOCUMENTS

| | | |
|---|---|---|
| WO | 2003098991 A2 | 12/2003 |
| WO | 2008070538 A2 | 6/2008 |
| WO | 2009023311 A2 | 2/2009 |
| WO | 2012049453 A2 | 4/2012 |
| WO | 2015032973 A1 | 3/2015 |

OTHER PUBLICATIONS

Tseng et al (US 2011/0117026 A1) in view of Jaiswal et al ("Nanoemulsion: an advanced mode of drug delivery system", 3 Biotech, vol. 5(2), p. 123-127 (2015)) (Year: 2015).*
Wu et al ("Topical transport of hydrophilic compounds using water-in-oil nanoemulsions", International Journal of Pharmaceutics, vol. 220 (issues 1-2), p. 63-75 (2001)) (Year: 2001).*
Zoonens et al ("Amphipols for Each Season", J. Membrane Biol, vol. 247, p. 759-796 (2014)) (Year: 2014).*
Tifrea et al ("Amphipols stabilize the Chlamydia major outer membrane protein and enhance its protective ability as a vaccine", Vaccine, vol. 29 (2011), p. 4623-4631) (Year: 2011).*
Rodriguez-Maranon et al ("Prediction of the membrane-spanning b-strands of the major outer membrane protein of Chlamydia", Protein Sci., vol. 11(7), (2002), p. 1854-61) (Year: 2002).*
Sharma et al ("Role of microemulsions in advanced drug delivery", Artificial Cells, Nanomedicine, and Biotechnology, vol. 44(4) (2015), p. 1177-1185) (Year: 2015).*
Jansen et al ("Structure-activity relations of water-in-oil vaccine formulations and induced antigen-specific antibody responses" Vaccine, vol. 23 (2005), p. 1053-1060) (Year: 2005).*
Dreier, et al. "Superresolution and Fluorescence Dynbamics Evidence Reveal That Intact Liposomes Do Not Cross the Human Skin Barrier," PLOS One, pp. 1-15 (Jan. 11, 2016) https://doi.org/10.1371/journal.pone.0146514.

(Continued)

*Primary Examiner* — Sin J Lee
(74) *Attorney, Agent, or Firm* — Todd Lorenz

(57) ABSTRACT

The invention provides topical formulations and methods comprising charged bioactive agents complexed with amphipol polymers for dermal and transdermal delivery, optionally further including TJ-modulating peptides.

15 Claims, 6 Drawing Sheets

(56) References Cited

OTHER PUBLICATIONS

Written Opinion and International Search Report with respect to PCT/US2018/017301 dated Mar. 28, 2018.
Extended European Search Report with respect to EP 18751388.2 dated Nov. 10, 2020.

* cited by examiner

TOPICAL FORMULATIONS AND METHODS

This application is a U.S. National Phase Application filed under 35 U.S.C. § 371 of PCT Application No. PCT/US2018/017301, filed Feb. 7, 2018, which claims priority to U.S. Provisional Application Ser. No. 62/456,066, Feb. 7, 2017, each of the applications of which are incorporated by reference in their entireties.

FIELD OF THE INVENTION

The invention provides compositions and methods for the efficient and effective dermal and transdermal delivery of bioactive agents, including charged and/or higher molecular weight biological molecules, as well as pharmaceutical, cosmetic and nutraceutical uses thereof.

BACKGROUND OF THE INVENTION

The outermost layer of human skin, the stratum corneum (SC), provides an essential protective physiological barrier against infection, dehydration, chemicals and mechanical stress, and consequently also poses very difficult challenges for the delivery of pharmaceutical, cosmetic and nutraceutical agents through the skin. The SC comprises multiple layers of corneocytes embedded in a lipid matrix, forming a lipophilic layer that allows only small, potent and moderately lipophilic molecules to partition across it passively and into the deeper layers of the skin. The intercellular lamellar lipid bilayer in the SC is particularly problematic for larger and/or more hydrophilic molecules to pass through such as, e.g. proteins and nucleic acids.

Moreover, the effective transdermal delivery of charged polypeptides and polynucleotides targeting sites deeper in subcutaneous tissue also faces another major barrier. The lipid bilayer in the SC creates the first impenetrable chemical barrier for effective dermal delivery, as noted above, while deeper in the stratified epidermal tissue the stratum granulosum formed by granulose keratinocytes is interconnected by a network of tight intercellular junctions (TJ's) which then block the path for further transdermal passage of larger molecules. TJ's are complex, ligand-gated protein structures, and are not responsive to lipid-dissolving chemical vectors such as the detergents and solvents conventionally used for passage through the lipophilic stratum corneum.

For the past 30+ years the prior art has focused almost exclusively on overcoming the SC barrier, and significant resources have been spent investigating a wide variety of chemical, physical and mechanical techniques including chemical penetration enhancers, iontophoresis, microneedles, sonophoresis, laser ablation, thermal ablation, radiofrequency ablation, jet injectors and electroporation. See, e.g. Prausnitz and Langer, Transdermal Delivery Systems, *Nat Biotechnol.* 2008 November; 26(11):1261-8.2. Chemical methods of enhancing transdermal drug delivery have more commonly been used and include the use of chemical enhancers to increase permeability of the SC. Although the penetration of some types of therapeutic agents can be increased using these chemical enhancers, high levels of certain enhancers can result in skin irritation and sensitization problems.

In particular, solvents such as ethanol, methanol, chloroform and acetone, as well as detergents, can extract SC barrier lipids and help permeabilize the SC. Morphological changes in the human SC following extensive exposure to such solvents include phase separation and derangement of lamellar bilayers in addition to the creation of defects in corneocytes. Surfactants, such as sodium dodecyl (lauryl) sulfate (SDS), and vehicles (e.g. propylene glycol) extract lipids, and create extensive expansion of pre-existing lacunar domains. Moreover, solvent-based penetration enhancers, such as azone, sulfoxides, urea and FFA, not only extract extracellular lipids, but also alter the SC lipid organization (phase behavior), thereby enhancing transdermal delivery and expanding intercellular domains. Unfortunately, however, these types of enhancers are only minimally effective in increasing the rate at which drugs permeate the skin, and may cause skin damage, irritation, sensitization, or the like. Moreover, and significantly, they are incapable of delivering higher molecular weight and/or charged bioactive agents.

In the prior art, for example, ionic detergents such as SDS, sodium lauryl sulfate, deoxycholate bile acids, and cetyltrimethylammonium bromide have been used academically to transfer proteins and polypeptides of various sizes (insulin, bovine serum albumin, lysozyme) between two aqueous phases across a lipid interphase. This technique, which utilizes ionic detergents for "hydrophobic ion pairing" of charged proteins to make them soluble in organic solvents, was originally developed for HPLC protein chromatography on reverse-phase resins. Despite its potential for transdermal protein drug delivery, however, this technology has a number of limitations and disadvantages.

First, the binding behavior of ionic detergents to proteins and polypeptides is dependent on the pH and ionic strength of the environment, which necessarily limits the available formulation choices for a pharmaceutical or cosmeceutical vector. If these conditions are not within narrow limits, the ionic detergents will cause unfolding and denaturation of the proteins rather than surface binding. The low critical micelle concentrations (CMC) of ionic detergents are also a problem since they place significant limitations on the amount of protein, in particular for larger proteins, that can be formulated into an ion-paired hydrophobic complex. Given their smaller size a high molar excess of detergents is typically needed to fully envelop the protein, and the larger the protein, the more detergent it takes. Correspondingly, however, the maximum amount of detergent that can form an ion-paired protein complex is limited by its CMC, because at and above the CMC detergent self-binding forming micelles are thermodynamically favored over ionic detergent-protein binding.

Lastly, and most critically for transdermal delivery in particular, the membranolytic and cytolytic properties of the ionic detergents often lead to skin tissue degradation and inflammatory reactions. Hence, effective formulations for transdermal delivery of large bioactive compounds based on ion-pairing with ionic detergents have never been successfully demonstrated outside of artificial experimental systems. Moreover, the few published cases of trans-lipid protein transfer provide little evidence for the functional and structural integrity of the proteins undergoing hydrophobic ion pairing.

Accordingly, there remains a need in the art for the development of safer and more effective dermal and transdermal delivery compositions and methods capable of delivering a wide range of cosmetic, pharmaceutical and nutraceutical agents, in particular charged and/or hydrophilic macromolecules (e.g., polypeptides and polynucleotides), through the skin barrier.

SUMMARY OF INVENTION

The present invention resolves this long-standing and unmet need in the art via the hydrophobic ion pairing of amphipol polymers with charged bioactive agents to facilitate their diffusion through the SC, but without the dissociating and ultimately damaging effects of conventional detergents. Topical formulations capable of both dermal and transdermal delivery are provided comprising an amphipol polymer non-covalently bound via intermolecular charge interaction (i.e. ionically paired) to the charged bioactive agent, thereby enhancing its lipophilicity and serving as a molecular chaperone through the lamellar lipid bilayer.

In one aspect, topical formulations for dermal delivery are provided comprising an amphipol polymer ionically paired with at least one charged bioactive agent in a dermatologically acceptable vehicle, e.g. a lotion, cream, ointment, gel, serum, emulsion (e.g., oil-in-water, water-in-oil, silicone-in-water, water-in-silicone, water-in-oil-in-water, oil-in-water-in-oil, oil-in-water-in-silicone, etc.), solution (e.g., aqueous or hydro-alcoholic solutions), anhydrous base (e.g., lipstick or a powder), mask, peel, eye jelly, and the like. Preferred amphipol polymers include, e.g. A8-35; PMAL-C8, PMAL-C12, and PMAL-C16. In some embodiments, the dermatologically acceptable vehicle comprises a nanoemulsion (generally from 1 to 200 nm, more preferably from 10-100 nm). In preferred embodiments exemplified herein, the dermatologically acceptable vehicle comprises a water-in-oil nanoemulsion, wherein the amphipol polymer/bioactive agent complex partitions to the oil phase of the nanoemulsion.

In additional embodiments, the subject compositions may further comprise water, a moisturizing agent or a humectant, a surfactant, a silicone-containing compound, a UV agent, a chelating agent, an essential oil, a skin lightener, a preservative, a thickening agent, a structuring agent, vitamin, a cosmetic ingredient, a pharmaceutical ingredient, an antioxidant, and/or other ingredients identified in this specification or known in the art.

In another aspect, the invention provides a method of dermally delivering a charged bioactive (e.g. cosmetic and/or pharmaceutical agent) across the SC comprising applying to the skin of a subject a topical formulation comprising an amphipol polymer ionically paired with at least one charged bioactive agent (e.g. hyaluronic acid, heparin, laminin, hyaluronidase inhibitors, RHAMM inhibitors, hyaluronan synthases, prostaglandin analogues, matrix metalloproteinase inhibitors, TNF-α antagonists, TGF-β, superoxide dismutase, growth factors, cytokines and/or matrikines) in a dermatologically acceptable vehicle.

In a specific embodiment, the present invention provides a method for improving skin appearance in a subject in need thereof comprising applying to the skin of a subject a topical formulation comprising a cosmetically effective amount of an amphipol polymer ionically paired with hyaluronan or a fragment or analogue thereof in a dermatologically acceptable carrier so as to improve the skin condition of the subject. In one embodiment, the cosmetic composition may further comprise an antioxidant, e.g. astaxanthin, BHT or tocopherol. In one embodiment, the cosmetic composition may further comprise a growth factor, cytokine and/or matrikine.

In another aspect, topical formulations for transdermal delivery are provided comprising combining the subject polymer/agent complexes together with at least one TJ-modulating peptide, which serves as a further chemical vector to facilitate passage of the charged bioactive agent through the tight intercellular junctions in the stratum granulosum. In one such embodiment, topical formulations for transdermal delivery are provided comprising an amphipol polymer ionically paired with at least one charged bioactive agent together with at least one TJ modulating peptide in a dermatologically acceptable vehicle, e.g. a lotion, cream, ointment, gel, serum, emulsion, solution, anhydrous base, mask, peel, eye jelly, and the like.

In preferred embodiments, the dermatologically acceptable vehicle is a nanoemulsion; still more preferably, a water-in-oil nanoemulsion, wherein the amphipol polymer/bioactive agent complex partitions to the oil phase of the nanoemulsion and the TJ-modulating peptide to the aqueous phase. In another preferred embodiment, alkylated TJ-modulating peptides are employed which partition together with the polymer-protein complex into the oil phase of the nanoemulsion. In yet another preferred embodiment, arginine/lysine-modified or aspartate/glutamate-modified TJ-modulating peptides are employed to enable amphipol ion-pairing of TJ-modulating peptides which partition together with the polymer-protein complex into the oil phase of the nanoemulsion.

In another aspect, the invention provides a method of transdermally delivering a charged cosmetic, pharmaceutical and/or nutraceutical agent comprising applying to the skin of a subject in need thereof a topical formulation comprising an amphipol polymer ionically paired with at least one charged bioactive agent (e.g. polypeptides, polynucleotides and other macromolecules including corticosteroids, hormones (e.g. human growth hormone, gonadotrophin hormones, etc.), chemodenervation agents (e.g. neurotoxins), vaccines, cytokines, TNF-α antagonists, TGF-β, antibodies, anti-fungals, anesthetics, insulin, opioids, and the like), together with at least one TJ-modulating peptide in a dermatologically acceptable vehicle.

In a specific embodiment, the present invention provides a method for improving the appearance of fine lines and wrinkles in a subject in need thereof, comprising topically applying an effective amount of an anti-wrinkle composition comprising an amphipol polymer ionically paired with a chemodenervation agent (e.g. neurotoxin protein, peptide or peptide mimetic), together with a TJ-modulating peptide in a dermatologically acceptable carrier to the skin of the subject so as to lessen and improve the appearance of fine lines and wrinkles.

The present invention also provides a method for treating a skin disorder in a subject in need thereof comprising applying to the skin of the subject a therapeutically effective amount of a therapeutic composition comprising an amphipol polymer ionically paired with at least one charged bioactive agent in a dermatologically acceptable carrier, and optionally further comprising at least one TJ-modulating peptide for transdermal delivery, so as to treat the skin disorder of the subject.

Also provided is a method of enhancing penetration of the skin by a charged cosmetic, pharmaceutical and/or nutraceutical agent comprising applying to the skin of a subject in need thereof a composition comprising an amphipol polymer ionically paired with at least one charged bioactive agent in a dermatologically acceptable vehicle, and optionally further comprising at least one TJ-modulating peptide for transdermal delivery, wherein the penetration of the charged bioactive agent is increased with respect to the penetration of the same agent in soluble form.

In another aspect, topical formulations and methods are provided for the dermal and transdermal delivery of chemodenervation agents (e.g. neurotoxin proteins, peptides or peptide mimetics), comprising an amphipol polymer ionically paired with at least one chemodenervation agent in a dermatologically acceptable carrier, and optionally further comprising at least one TJ-modulating peptide for transdermal delivery.

In another aspect, topical formulations and methods are provided for the dermal and transdermal delivery of growth factors and other hormones (e.g. human growth hormone, gonadotrophin, etc.), comprising an amphipol polymer ionically paired with the hormone in a dermatologically acceptable carrier, and optionally further comprising at least one TJ-modulating peptide for transdermal delivery.

In another aspect, topical formulations and methods are provided for the dermal and transdermal delivery of anti-fungal agents (e.g. terbinafine, itraconazole, micronazole nitrate, thiapendazole, tolnaftate, clotrimazole and griseofulvin), comprising an amphipol polymer ionically paired with the anti-fungal agent in a dermatologically acceptable carrier, and optionally further comprising at least one TJ-modulating peptide for transdermal delivery.

In another aspect, topical formulations and methods are provided for the dermal and transdermal delivery of vaccines (e.g. flu/influenza vaccines, vaccines for hepatitis A, B, C, the measles-mumps-rubella (MMR) vaccine, the tenaus-diphtheria vaccine, the varicella (chickenpox) vaccine, the pneumococcal vaccine, the meningococcal conjugate vaccine, and the like), comprising an amphipol polymer ionically paired with the vaccine in a dermatologically acceptable carrier, and optionally further comprising at least one TJ-modulating peptide for transdermal delivery. Additional additive ingredients such as adjuvants can be co-formulated or co-administered, as appropriate.

In another aspect, topical formulations and methods are provided for the dermal and transdermal delivery of growth factors and other hormones such as, e.g., human growth hormone, estrogens, progesterone and other progestogens, antiandrogens, antiestrogens, androgens and anabolic agents, 5-alpha reductase inhibitors, pituitary hormones and their active derivatives or analogs, thyroid hormones, pituitary inhibitors, ovulation inducers, and hypoglycaemic agents, comprising an amphipol polymer ionically paired with at least one hormone in a dermatologically acceptable carrier, and optionally further comprising at least one TJ-modulating peptide for transdermal delivery. A single hormone may be used, or alternatively, a combination of hormones may be used.

In another aspect, topical formulations and methods are provided for the dermal and transdermal delivery of therapeutic nucleic acids (e.g., oligonucleotides, miRNA, shRNA, siRNA, DNA, RNA, mRNA, cDNA, double stranded nucleic acid, single stranded nucleic acid, antisense sequence, etc.), comprising an amphipol polymer ionically paired with the therapeutic nucleic acid in a dermatologically acceptable carrier, and optionally further comprising at least one TJ-modulating peptide for transdermal delivery. In some embodiments, the DNA is a vector comprising an expression construct for expression of one or more therapeutic polynucleotides or one or more polynucleotides encoding a therapeutic gene product.

The present invention now will be described more fully hereinafter with reference to the accompanying drawings, in which certain embodiments of the invention are shown. Indeed, the invention may be embodied in many different forms and should not be construed as limited to the embodiments set forth herein; rather, these embodiments are provided so that this disclosure will satisfy applicable legal requirements.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
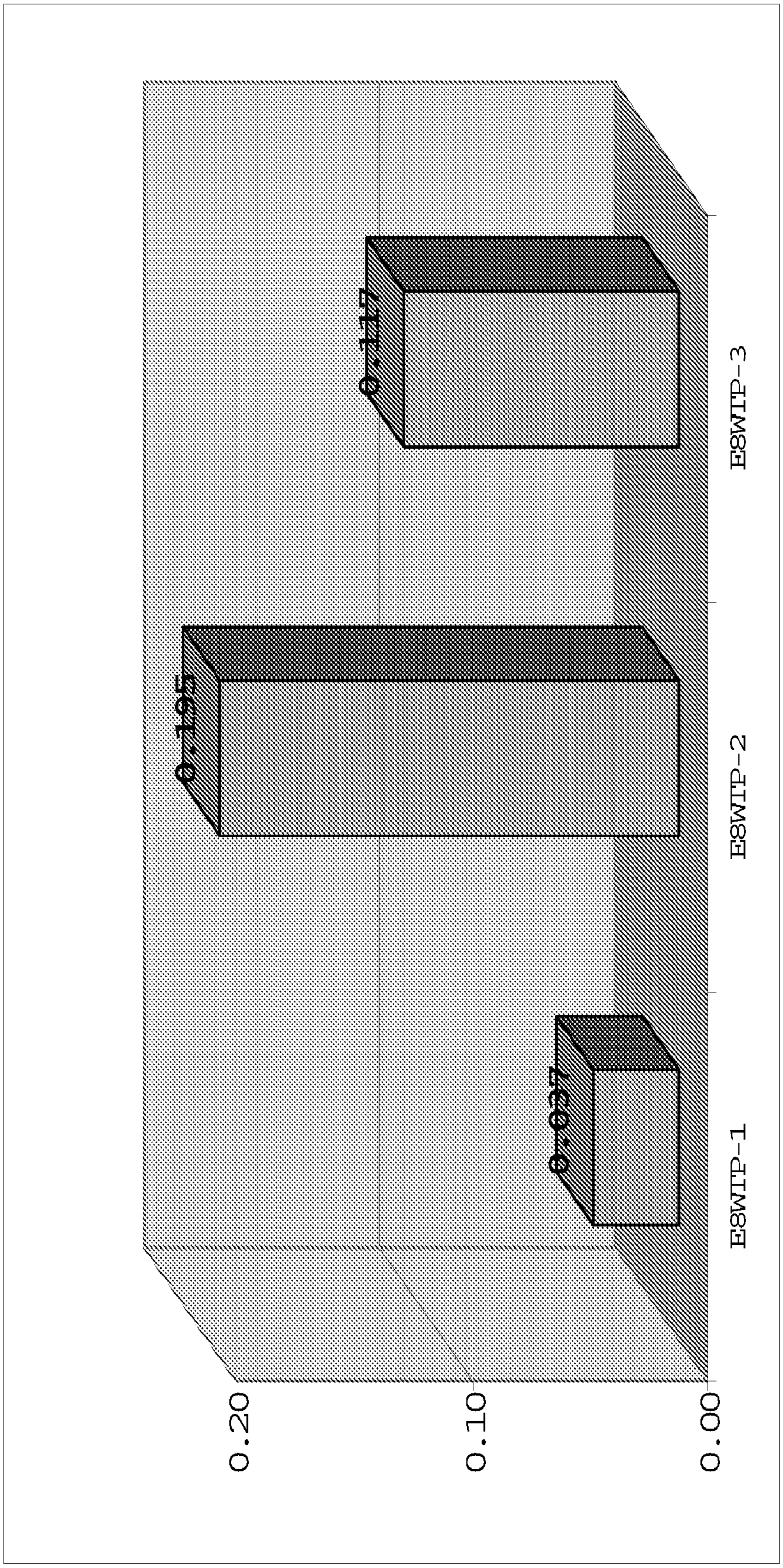
FIG. 1 is a graph showing the respective transdermal flux rates of three different formulations as measured in a Franz cell diffusion assay. The label on top of each bar shows the rate of transcutaneous transfer of MCPT-201 into the Franz cell receiving chamber measured in mg per hour per $cm^2$. The label on each bar shows the total amount of MCPT-201 transferred through 0.64 $cm^2$ of porcine skin during the indicated incubation time.

In one aspect, topical formulations for effective and efficient dermal delivery are provided comprising an amphipol polymer ionically paired with at least one charged bioactive agent in a dermatologically acceptable vehicle, e.g. a lotion, cream, ointment, gel, serum, emulsion (e.g., oil-in-water, water-in-oil, silicone-in-water, water-in-silicone, water-in-oil-in-water, oil-in-water-in-oil, oil-in-water-in-silicone, etc.), solution (e.g., aqueous or hydro-alcoholic solutions), anhydrous base (e.g., lipstick or a powder), mask, peel, eye jelly, and the like. In another aspect, the subject formulations are adapted for transdermal delivery, and further comprise at least one TJ-modulating peptide to facilitate passage of the charged bioactive agent through the tight junctions in the stratum granulosum.

The inventive compositions comprise a dermatologically acceptable vehicle or carrier for the subject amphipol polymer/charged bioactive agent complexes. The compositions can also include one or more of the following additional ingredients: water, a moisturizing agent or a humectant, a surfactant, a silicone-containing compound, a UV agent, a chelating agent, an essential oil, a skin lightener, a preservative, a thickening agent, a structuring agent, a vitamin, a cosmetic ingredient, a pharmaceutical ingredient, an antioxidant, and/or other ingredients identified in this specification or known in the art, or any combination of such ingredients or mixtures of such ingredients.

Kits that include the compositions of the present invention are also contemplated. In certain embodiments, the composition is comprised in a container. The container can be a bottle, dispenser, or package, and may further include appropriate instructions for use. The container can dispense a pre-determined amount of the composition, e.g. a daily amount. The container can include indicia on its surface, which can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a freshener, a toner, a sunscreen, a mask, an anti-aging product, a deodorant, an antiperspirant, a perfume, a cologne, etc.

In some embodiments, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Definitions

"Lipophilic" as used herein refers to compounds that dissolve in fats, oils, lipids, and non-polar solvents, such as organic solvents. Lipophilic compounds are sparingly soluble or insoluble in water. Thus, lipophilic compounds are generally hydrophobic.

As used herein, "hydrophilic" is a physical property of a molecule that is capable of hydrogen bonding with a water ($H_2O$) molecule and is soluble in water and other polar solvents. The terms "hydrophilic" and "polar" can be used interchangeably. Hydrophilic characteristics generally derive from the presence of polar or charged groups, such as carbohydrates, phosphate, carboxylic, sulfato, amino, sulfhydryl, nitro, hydroxy and other like groups.

Conversely, the term "hydrophobic" is a physical property of a molecule that is repelled from a mass of water and can be referred to as "nonpolar," or "apolar," all of which are terms that can be used interchangeably with "hydrophobic." Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s).

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The term "about," when referring to a value is meant to encompass variations of, in some embodiments +/−50%, in some embodiments +/−20%, in some embodiments +/−10%, in some embodiments +/−5%, in some embodiments +/−1%, in some embodiments +/−0.5%, and in some embodiments +/−0.1% from the specified amount, as such variations are appropriate to perform the disclosed methods or employ the disclosed compositions.

"Topical application" means to apply or spread a composition onto the surface of the skin and/or lips. A "topical formulation" includes compositions suitable for topical application to the skin and/or lips. Such compositions are typically dermatologically acceptable in that they do not have undue toxicity, incompatibility, instability, allergic response, and the like, when applied to lips or skin. The topical formulations of the present invention preferably have a selected viscosity to avoid significant dripping or pooling after application to the skin.

The terms "inhibiting," "reducing" or "lessening" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or macromolecules such as hyaluronic acid) to achieve a desired result.

"Treating" or any variation of this term includes any measurable improvement in a disease, condition, or symptom that is being treated or is associated with the disease, condition, or symptom being treated.

"Preventing" or any variation of this term means to slow, stop, or reverse progression toward a result. The prevention may be any slowing of the progression toward the result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive and open-ended and do not exclude additional, un-recited elements or method steps.

The compositions and methods for their use can "comprise," "consist essentially of," or "consist of" any of the ingredients or steps disclosed throughout the specification.

Amphipols

Amphipols are short amphipathic polymers originally developed to keep individual membrane proteins water soluble in their native state in the form of small hydrophilic complexes (see, e.g., Tribet et al. Amphipols: polymers that keep membrane proteins soluble in aqueous solutions, *Proc Natl Acad Sci USA.* 93(26):15047-50 (1996); Popot et al. Amphipols: polymeric surfactants for membrane biology research *Cell Mol Life Sci.* 60(8):1559-74 (2003); Chae et al., A new class of amphiphiles bearing rigid hydrophobic groups for solubilization and stabilization of membrane proteins *Chemistry* 18(31):9485-9490 (2012); Della Pia et al., Functionalized amphipols: a versatile toolbox for applications of membrane proteins in synthetic biology *J. Membrane Biol.* 247(9-10):815-816 (2014). The molecules were devised to bind to the transmembrane surface of membrane proteins in a noncovalent but quasi-irreversible manner, which was initially achieved by modifying surfactants to carry a large number of hydrophobic chains. To date, they have never been employed outside of academic synthetic biology.

The present inventor has determined that this particular class of polymers can be advantageously used in the effective and efficient dermal and transdermal delivery of charged and/or higher molecular weight biological molecules, including polypeptides, polynucleotides and other hydrophobic macromolecules. Topical formulations capable of both dermal and transdermal delivery are provided comprising an amphipol polymer non-covalently bound via intermolecular charge interaction (i.e. ionically paired) to the desired bioactive agent, thereby enhancing the lipophilicity of the bioactive agent and acting as a molecular chaperone through the lamellar lipid bilayer. Without being bound by theory, once the hydrophobic polymer-agent complex contacts electrolytes at physiological pH in the extracellular matrix beneath the SC, the ionic pairing between the agent (e.g. protein) and the polymer dissolves and the bioactive agent is then released as a hydrophilic compound.

Amphipol polymers suitable for use herein are either ionic polymers, i.e. polymers comprising charged or ionizable groups alternating with lipophilic groups or side chains, or alternatively amphipathic polymers where all of the hydrophilic groups are ionic groups engaging in ion-pairing with opposite charges on the surface of the protein. Preferably, the molecular dimensions and flexibility of the amphipol polymers enable them to ionically pair at multiple points with the bioactive agent, ensuring that the desorption kinetics are slow and that ionic pairing between the amphipol polymer and the bioactive agent is favored. Preferred amphipol polymers for use in the subject formulations and methods include, e.g. A8-35; PMAL-C8, PMAL-C12, and PMAL-C16 (available from Anatrace, Inc. Maumee, Ohio), the chemical structures of which are set forth below. Also contemplated for use herein are suitable derivatives and/or functional variants thereof (see, e.g., Chae et al. and Della Pia et al., supra; see also WO 1998/027434; WO 2008/058963; and U.S. Pat. Nos. 8,815,263 and 8,207,263, the disclosures of which are incorporated by reference herein in their entireties), whether now known or subsequently developed for this or any other purpose.

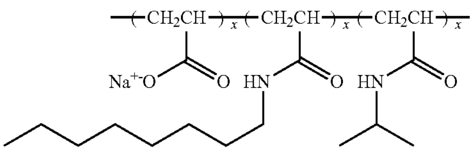

Amphiphol A835:

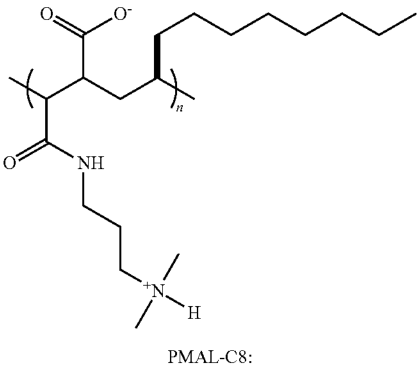

PMAL-C8:

-continued

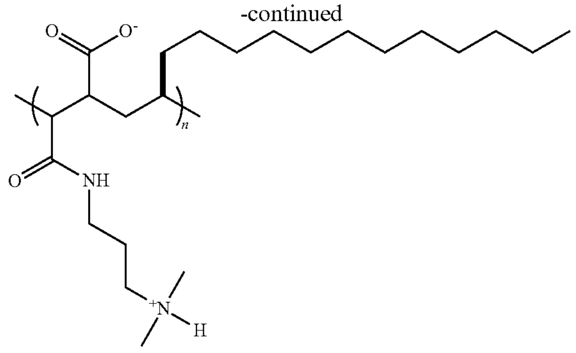

PMAL-C12:

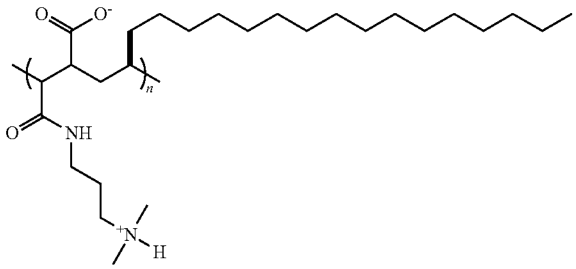

PMAL-C16:

x = 0.35, y = 0.25, z = 0.40

The choice of a suitable amphipol polymer will depend on the net surface charge and the surface charge distribution of the bioactive agent of interest, which is readily determinable by the skilled artisan. For molecules having zero net surface charge but both positive and negative surface charge distribution, for example, or for molecules having a slightly negative net surface charge, a zwitterionic amphipol polymer such as the commercially-available PMAL series can be used. For molecules having a net negative charge, an amphipol polymer having a net positive charge can be used. Alternatively, macromolecules with a negative net charge can also be enveloped with zwittionic amphipols provided the formation of the polymer/molecule complex is performed under a pH that favors preferential ionization of its cationic groups.

The amphipol polymers of the subject invention provide significant advantages over the simple ionic detergents conventionally used in the prior art, since they do not possess the membranolytic, cytolytic and protein-denaturing properties of detergents that can damage the epidermis and cause inflammation. In addition, amphipol polymers do not have the CMC limitations of typical ionic detergents that significantly limit the amount of detergent that can be used to envelop a protein or other macromolecule.

TJ-Modulating Peptides

TJ-modulating peptides constitute the secondary transdermal vector in the methods and compositions of this invention, to improve the effective transdermal passage of the bioactive agent. Without being bound by theory, they take on the function of transiently increasing the permeability of intercellular TJ's in the stratum granulosum, stratum spinosum and stratum basale of the epidermis by competing directly with protein-protein interactions between protein complexes (occludins and claudins) in TJ's.

TJ-modulating peptides suitable for use in the methods and compositions of the invention include, but are not limited to: transdermal peptide NH2-ACSSSPSKHCG- COOH (Chen et al., *Nat Biotechnol.* 2006 April; 24(4):455-60)); synthetic biomimetic peptide analogues of occludin's first and second extracellular loops such as NH2-SNYYGSGLS-COOH, NH2-DRGYGTSLLGGSVG-COOH; and synthetic biomimetic peptide analogues of claudin-actin peptides. The above listed TJ-modulating peptides comprise either all L-amino acid, all D-amino acid or mixed L-/D-amino acid derivatives, alkyl-(C8-C14)-amino-acid derivatives, C- or N-terminally alkylated or cholesterol-modified derivatives. In some embodiments, they can be formulated in combination with other, non-peptide derived TJ-modulating agents such as bile acids and $Ca^{2+}$ chelators.

Bioactive Agents

Bioactive agents finding advantageous use in the subject compositions and methods include polypeptides, polynucleotides, and other charged and/or hydrophobic macromolecules.

For cosmetic purposes, the charged bioactive agent may advantageously comprise hyaluronic acid, heparin, laminin, hyaluronidase inhibitors (e.g. McCook et al., *Clin Cosmet Investig Dermatol* 8:443-8 (2015)), RHAMM inhibitors (e.g. Tolg et al. *Am. J. Path.* 181:1250-70 (2012), hyaluronan synthases (e.g. Siiskonen et al. *Front. Immunol.* 6:43 (2015)), prostaglandin analogues (e.g. bimatoprost, latanoprost, etc.), matrix metalloproteinase inhibitors (e.g. U.S. Patent Publication No. 2016/0326530; U.S. Patent Publication No. 2006/0074108), TNF-α antagonists (e.g. U.S. Pat. No. 5,993,833 and WO 2006/113487), TGF-β (e.g. Ehrlich et al., Dermatol. Surg. 32(5):618-25 (2006)); superoxide dismutase, growth factors (e.g. human growth hormone), cytokines and matrikines (see, e.g. Aldag et al., *Clin. Cosmet Investig Dermatol* 9:411-19 (2016)), as well as mimics, variants and derivatives thereof.

For pharmaceutical purposes, the bioactive agent may advantageously comprise corticosteroids, hormones (e.g. human growth hormone, gonadotrophin, etc.) chemodenervation agents (e.g. neurotoxin proteins, peptides or peptide mimetics), vaccines, cytokines, TNF-α antagonists, TGF-β, antibodies, anti-fungals, anesthetics, insulin, opioids, and the like), together with at least one TJ-modulating peptide in a dermatologically acceptable vehicle.

In some embodiments, topical formulations and methods are provided for the dermal delivery of hyaluronic acid, comprising an amphipol polymer ionically paired with hyaluronic acid or a fragment or derivative thereof in a dermatologically acceptable carrier. Hyaluronic acid is a ubiquitous natural polysaccharide and a natural constituent of the dermis, where it plays an important role in the hydration and elasticity of the skin. It is highly water-soluble and hence very difficult to deliver through the SC. Its potential use and value as a key macromolecule in skin aging is very well-established, and effective dermal delivery has been a long-sought and unmet need. See, e.g. Stern and Maibach, *Clin. Dermatol.* 26:106-122 (2008).

The formulations according to the invention may also comprise an inhibitor of hyaluronic acid degradation. The term "inhibitor of hyaluronic acid degradation" means a compound capable of reducing, or even blocking, either the extracellular or the intracellular catabolism of hyaluronic acid, preferably a compound capable of reducing, or even blocking, the extracellular catabolism of hyaluronic acid, more preferably a compound capable of inhibiting the extracellular hyaluronidase present in the skin. Among the inhibitors of hyaluronic acid degradation are glycyrrhizin or glycyrrhetinic acid, and mimics, derivatives and/or variants thereof, as well as the sodium copper chlorophyllin complex and chlorophyllin analogs disclosed by McCook et al., supra. Similarly, the formulations according to the invention may also comprise one or more hyaluronan synthases, including, e.g., HAS-1, HAS-2, and/or HAS-3 (see, e.g., Siiskonen et al., supra; Papakonstantinou et al., *Dermato-Endocronol* 4(3): 253-58 (2012).

In some embodiments, topical formulations and methods are provided for the dermal and transdermal delivery of chemodenervation agents (e.g. neurotoxin proteins, peptides or peptide mimetics), comprising an amphipol polymer ionically paired with at least one chemodenervation agent in a dermatologically acceptable carrier, and optionally further comprising at least one TJ-modulating peptide for transdermal delivery. Neurotoxin proteins suitable for use in the subject invention include, e.g., bacterial neurotoxins such as those derived from *Clostridium botulinum, Clostridium butyricum*, or *Clostridium beratti*; conotoxins derived from Conus marine snails (See, e.g. U.S. Pat. No. 9,566,227, the disclosure of which is expressly incorporated by reference herein); α-neurotoxins derived from a wide variety of snake species including alpha-bungarotoxin (see, e.g., WO 2009/05585, the disclosure of which is expressly incorporated by reference herein), and waglerin-1 and/or -2 (see, e.g., U.S. Pat. No. 9,550,808, the disclosure of which is expressly incorporated by reference herein) as well as fragments, mimics and/or derivatives thereof. In one embodiment, the invention comprises an amphipol polymer ionically paired with at least one α-neurotoxin together with at least one TJ-modulating peptide in a dermatologically acceptable carrier. In one embodiment, invention comprises an amphipol polymer ionically paired with at least one botulinum toxin, which may be a botulinum toxin type A, type B, type C1, type D, type E, type F, or type G together with at least one TJ-modulating peptide in a dermatologically acceptable carrier. In another embodiment, the invention comprises an amphipol polymer ionically paired with at least one alpha-neurotoxin or waglerin-1, or a fragment or derivative thereof, together with at least one TJ-modulating peptide in a dermatologically acceptable carrier.

In some embodiments, topical formulations and methods are provided for the dermal and transdermal delivery of anti-fungal agents (e.g. terbinafine, itraconazole, miconazole nitrate, thiapendazole, tolnaftate, clotrimazole and griseofulvin), comprising an amphipol polymer ionically paired with the anti-fungal agent in a dermatologically acceptable carrier, and optionally further comprising at least one TJ-modulating peptide for transdermal delivery.

In some embodiments, topical formulations and methods are provided for the dermal and transdermal delivery of vaccines (e.g. flu/influenza vaccines, vaccines for hepatitis A, B, C, the measles-mumps-rubella (MMR) vaccine, the tetanus-diphtheria vaccine, the varicella (chickenpox) vaccine, the pneumococcal vaccine, the meningococcal conjugate vaccine, and the like), comprising an amphipol polymer ionically paired with the vaccine in a dermatologically acceptable carrier, and optionally further comprising at least one TJ-modulating peptide for transdermal delivery. Additional additive ingredients such as adjuvants can be co-formulated or co-administered, as appropriate.

In some embodiments, topical formulations and methods are provided for the dermal and transdermal delivery of growth factors and other hormones such as, e.g., Human Growth Hormone, Estrogens (e.g. estradiol, estriol, estrone, ethinyloestradiol, mestranol, stilboestrol, dienestrol, epiestriol, estropipate and zeranol); Progesterone and other progestagens (e.g. allyloestrenol, dydrgesterone, lynoestrenol, norgestrel, norethyndrel, norethisterone, norethisterone acetate, gestodene, levonorgestrel, medroxyprogesterone and megestrol); Antiandrogens (e.g. cyproterone acetate and danazol); Antiestrogens such as tamoxifen and epitiostanol and the aromatase inhibitors, exemestane and 4-hydroxy-androstenedione and its derivatives; Androgens and anabolic agents (e.g. testosterone, methyltestosterone, clostebol acetate, drostanolone, furazabol, nandrolone oxandrolone, stanozolol, trenbolone acetate, dihydro-testosterone, 17-.alpha.-methyl-19-nortestosterone and fluoxymesterone); 5-alpha reductase inhibitors such as finasteride, turosteride, LY-191704 and MK-306; Pituitary hormones and their active derivatives or analogs such as corticotrophin, thyrotropin, follicle stimulating hormone (FSH), luteinising hormone (LH) and gonadotrophin releasing hormone (GnRH); Thyroid hormones (e.g. calcitonin, thyroxine and liothyronine and antithyroid agents such as carbimazole and propylthiouracil); miscellaneous agents such as octreotide; pituitary inhibitors such as bromocriptine; ovulation inducers such as clomiphene; and Hypoglycaemic agents (e.g. insulin, chlorpropamide, glibenclamide, gliclazide, glipizide, tolazamide, tolbutamide, metformin, pioglitazone, rosiglitazone, and troglitazone) comprising an amphipol polymer ionically paired with at least one hormone in a dermatologically acceptable carrier, and optionally further comprising at least one TJ-modulating peptide for transdermal delivery. A single hormone may be used, or alternatively, a combination of hormones may be used.

In some embodiments, topical formulations and methods are provided for the dermal and transdermal delivery of corticosteroids (e.g. betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide), comprising an amphipol polymer ionically paired with the corticosteroid in a dermatologically acceptable carrier, and optionally further comprising at least one TJ-modulating peptide for transdermal delivery. A single corticosteroid may be used, or alternatively, a combination of corticosteroids may be used.

In some embodiments, topical formulations and methods are provided for the dermal and transdermal delivery of non-steroidal anti-inflammatory drugs (NSAIDs) (e.g. aspirin, salsalate, diflunisal, ibuprofen, ketoprofen, nabumetone, piroxicam, naproxen, diclofenac, indomethacin, sulindac, tolmetin, etodolac, detorolac, oxaprozin, celecoxib and pharmaceutically acceptable derivatives thereof), comprising an amphipol polymer ionically paired with the NSAID in a dermatologically acceptable carrier, and optionally further comprising at least one TJ-modulating peptide for transdermal delivery. A single NSAID may be used, or alternatively, a combination of NSAIDs may be used.

In some embodiments, topical formulations and methods are provided for the dermal and transdermal delivery of anesthetics (e.g. benzocaine, lidocaine, tetracaine, bupivacaine, cocaine, etidocaine, mepivacaine, pramoxine, prilocalne, procaine, cnloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof), comprising an amphipol polymer ionically paired with the anesthetic in a dermatologically acceptable carrier, and optionally further comprising at least one TJ-modulating peptide for transdermal delivery.

In some embodiments, topical formulations and methods are provided for the dermal and transdermal delivery of therapeutic nucleic acids (e.g., oligonucleotides, miRNA, shRNA, siRNA, DNA, RNA, mRNA, cDNA, double stranded nucleic acid, single stranded nucleic acid, antisense sequences, etc.), comprising an amphipol polymer ionically paired with the therapeutic nucleic acid in a dermatologically acceptable carrier, and optionally further comprising at least one TJ-modulating peptide for transdermal delivery. In some embodiments, the DNA is a vector comprising an expression construct for expression of one or more therapeutic polynucleotides or one or more polynucleotides that encodes a therapeutic gene product.

Also contemplated for delivery herein are nutraceutical agents such as, e.g., vitamins, minerals, and amino acids, as well as herbal remedies such as neem, turmeric, sandal, etc.

In addition, the topical dermatologically acceptable carrier may also comprise additional ingredients generally used in cosmetics and skin preparations. Non-limiting examples of such ingredients include collagen, alpha hydroxyacids, alpha ketoacids, polymeric hydroxyacids, moisturizers, marine extract, and antioxidants such as ascorbic acid (vitamin C), tocopherol (Vitamin E), astaxanthine, and retinol (vitamin A), superoxide dismutase and/or cosmetically acceptable salts, esters, amides, or other derivatives thereof. Also contemplated for use herein are stratum corneum lipids, such as ceramides, cholesterol and free fatty acids, for improved skin barrier repair. Cosmetic ingredients include those that are capable of improving oxygen supply in skin, as well as plant extracts, such as horsetail extract, horse chestnut extract, rose extract and lavender extract. Other non-limiting examples of suitable ingredients include long-chain fatty acid esters of retinol or retinol derivatives or analogues, such as those in which the acyl moiety of the ester is selected from myristic acid, palmitic acid, and stearic acid.

Yet other non-limiting examples of suitable ingredients include sunscreens, such as those selected from octyl methoxycinnamate, p-aminobenzoic acid, ethyl p-aminobenzoate, isobutyl p-aminobenzoate, glyceryl aminobenzoate, p-dimethylaminobenzoic acid, methyl anthranilate, menthyl anthranilate, phenyl anthranilate, benzyl anthranilate, phenylethyl anthranilate, linalyl anthranilate, terpinyl anthranilate, cyclohexenyl anthranilate, amyl salicylate, phenyl salicylate, benzyl salicylate, menthyl salicylate, glyceryl salicylate, dipropyleneglycol salicylate, methyl cinnamate, benzyl cinnamate, .alpha.-phenyl cinnamonitrile, butyl cinnamoylpyruvate, umbelliferone, methylacetoumbelliferone, esculetin, methylesculetin, daphnetin esculin, daphnin, diphenylbutadiene, stilbene, dibenzalacetone, benzalacetophenone, sodium 2-naphthol-3,6-disulfonate, sodium 2-naphthol-6,8-disulfonate, dihydroxynaphthoic acid, salts of dihydroxynaphthoic acid, o-hydroxybiphenyldisulfonates, p-hydroxybiphenyldisulfonates, 7-hydroxycoumarin, 7-methylcoumarin, 3-phenylcoumarin, 2-acetyl-3-bromoindazole, phenylbenzoxazole, methylnaphthoxazole, arylbenzothiazoles, quinine bisulfate, quinine sulfate, quinine chloride, quinine oleate, quinine tannate, 8-hydroxyquinoline salts, 2-phenylquinoline, hydroxy-substituted benzophenones, methoxy-substituted benzophenones, uric acid, vilouric acid tannic acid, tannic acid hexaethylether, hydroquinone, oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyldibenzoylmethane.

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

The compositions can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25.degree. C.).

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

In addition to the specific combination of ingredients disclosed by the inventors, the compositions can also include additional ingredients such as cosmetic ingredients and pharmaceutical ingredients. Non-limiting examples of these additional ingredients are described in the following subsections.

Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., Aloe vera, chamomile, cucumber extract, *Ginkgo biloba, ginseng*, and rosemary), anti-microbial agents, antioxidants (e.g., astaxanthin, BHT, superoxide dismutase and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, plankton extract, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene di camphor sulfonic acid, di sodium phenyl dibenzimidazole tetra sul fonate, di ethyl amino hydroxybenzoyl hexyl benzoate, bis di ethyl amino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, plankton extract, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, Aloe barbadensis, Aloe barbadensis extract, Aloe barbadensis gel, Althea *officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia* cerifera) wax, canola oil, caprylic/capric triglyceride, cardamom (*Elettaria cardamomum*) oil, carnauba (*Copernicia* cerifera) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8.degree. C.12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

Antioxidants

Non-limiting examples of antioxidants that can be used with the compositions of the present invention include astaxanthin, acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, poly silicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160.degree. to 240.degree. C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

Pharmaceutical Ingredients

Pharmaceutical ingredients are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti-seborrheic agents, biologically active proteins and peptides, burn treatment agents, cauterizing agents, depigmenting agents, depilatories, diaper rash treatment agents, enzymes, hair growth stimulants including prostaglandins and analogs thereof, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreen agents, transdermal actives, nasal actives, vaginal actives, wart treatment agents, wound treatment agents, wound healing agents, etc.

Accordingly, in some embodiments the subject compositions comprise one or more pharmaceutical ingredients selected from the group consisting of: androgens, estrogens, selective estrogen receptor modulators, aromatase inhibitors, gonadotropins, progesterone, progestins, selective progesterone receptor modulators, antiprogestogen, antigonadotropins, GnRH: (receptor) agonists, antidiarrhoeals, cardiovascular system agents, antihypertensives, calcium channel blockers, proton pump inhibitors, antiarrhyrthmics, antiangina, beta-adrenergic blocking agents, cardiotonic glycosides, adrenergic stimulants, vasodilators, antimigraine preparations, anticoagulants, haemostatic agents, analgesics, antipyretics, hypnotics, antianxiety, neuroleptic and antipsychotic drugs, antidepressants, CNS stimulants such as caffeine, anti-alzheimer's agents, antiparkinson agents, lipid regulating drugs, anticonvulsants, antiemetics, antinauseants, non-steroidal antiinflammatory agents, antirheumatoid, muscle relaxants, agents used in gout and hyperuricaemia, diuretics, antidiuretics, obstetric drugs, prostaglandins, antimicrobials, antituberculosis drugs, antimalarials, antiviral agents, anthelmintics, cytotoxic agents, anorectics, agents used in hypercalcaemia, antitussives, expectorants, decongestants, bronchospasm relaxants, antihistamines, local anaesthetics, stratum corneum lipids, H2-receptor antagonists, neuromuscular blocking agents, smoking cessation agents, insecticides and other pesticides, dermatological agents, allergens, nutraceutically active compounds, keratolytics, psychicenergisers, anti-acne agents, anti-psoriasis agents, anti-itch agents, anticholinergic agents, and mixtures thereof.

Pharmaceutical ingredients that may be used in the transdermal drug delivery system of the present invention include any locally applied active agents which are compatible with the composition of the present invention and which can be delivered through the skin with the assistance of the composition to achieve a desired effect. Exemplary embodiments include Antidiarrheals (e.g. diphenoxylate, loperamide and hyoscyamine) Antihypertensives (e.g. hydralazine, minoxidil, captopril, enalapril, clonidine, prazosin, debrisoquine, diazoxide, guanethidne, methyldopa, reserpine, trimetaphan); Calcium channel blockers (e.g. as diltiazem, felodopine, amlodipine, nitrendipine, nifedipine and verapamil); Antiarrhyrthmics (e.g. amiodarone, flecainide, disopyramide, procainamide, mexiletene and quinidine); Antiangina agents (e.g. glyceryl trinitrate, erythritol tetranitrate, pentaerythritol tetranitrate, mannitol hexanitrate, perhexilene, isosorbide dinitrate and nicorandil): Beta-adrenergic blocking agents (e.g. alprenolol, atenolol, bupranolol, carteolol, labetalol, metoprolol, nadolol, nadoxolol, oxprenolol, pindolol, propranolol, sotalol, timolol and timolol maleate); Cardiotonic glycosides (e.g. digoxin and other cardiac glycosides and theophylline derivatives); Adrenergic stimulants (e.g. adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine); Vasodilators (e.g. cyclandelate, isoxsuprine, papaverine, dipyrimadole, isosorbide dinitrate, phentolamine, nicotinyl alcohol, codergocrine, nicotinic acid, glyceryl trinitrate, pentaerythritol tetranitrate and xanthinol); Antimigraine preparations (e.g. ergotamine, dihydroergotamine, methysergide, pizotifen and sumatriptan); Anticoagulants and thrombolytic agents (e.g. warfarin, dicoumarol, low molecular weight heparins such as enoxaparin; streptokinase and its active derivatives; Hemostatic agents (e.g. aprotinin, tranexamic acid and protamine); Analgesics and antipyretics including opioids (e.g. aspirin (acetylsalicylic acid), paracetamol, phenazone, fentanyl, alfentanil, sufentanil, buprenorphine, dextromoramide, dextropropoxyphene, hydromorphone, methadone, morphine, oxycodone, papaveretum, pentazocine, pethidine, phenoperidine, codeine and dihydrocodeine); Hypnotics and sedatives such as barbiturates (e.g., amylobarbitone, butobarbitone and pentobarbitone) and other hypnotics and sedatives such as choral hydrate, chlormethiazole, hydroxyzine and meprobamate; Antianxiety agents (e.g. benzodiazepines, alprazolam, bromazepam, chlordiazepoxide, clobazam, chlorazepate, diazepam, flunitrazepam, flurazepam, lorazepam, nitrazepam, oxazepam, temazepam and triazolam); Neuroleptic and antipsychotic drugs such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium; Antidepressants (e.g. tricyclic antidepressants including amitryptyline, clomipramine, desipramine, dothiepin, doxepin, imipramine, nortriptyline, opipramol, protriptyline and trimipramine; tetracyclic antidepressants including mianserin; monoamine oxidase inhibitors including isocarboxazid, phenelizine, tranylcypromine and moclobemide and selective serotonin re-uptake inhibitors including fluoxetine, paroxetine, citalopram, fluvoxamine and sertraline); CNS stimulants (e.g. caffeine); Anti-alzheimer's agents (e.g. tacrine); Antiparkinson agents (e.g. amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923); Anticonvulsants (e.g. phenytoin, valproic acid, primidone, phenobarbitone, methylphenobarbitone and carbamazepine, ethosuximide, methsuximide, phensuximide, sulthiame and clonazepam); Antinauseants (e.g. phenothiazines, prochloperazine, thiethylperazine and 5HT-3 receptor antagonists including ondansetron and granisetron and others such as dimenhydrinate, diphenhydramine, metoclopramide, domperidone, hyoscine, hyoscine hydrobromide, hyoscine hydrochloride, clebopride and brompride); Muscle relaxants (e.g. baclofen, diazepam, cyclobenzaprine hydrochloride, dantrolene, methocarbamol, orphenadrine and quinine); Antirheumatoid agents (e.g. penicillamine, aurothioglucose, sodium aurothiomalate, methotrexate and auranofin); Agents used in gout and hyperuricaemia such as allopurinol, colchicine, probenecid and sulphinpyrazone.

Also contemplated for use herein are non-steroidal anti-inflammatory agents including their racemic mixtures or individual enantiomers where applicable (e.g. ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol and ketorolac). Additional non-steroidal anti-inflammatory agents which can be formulated in the subject compositions include salicylamide, salicylic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloide, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

Also contemplated for use herein are hormones, including Human Growth Hormone, Estrogens (e.g. estradiol, estriol, estrone, ethinyloestradiol, mestranol, stilboestrol, dienestrol, epiestriol, estropipate and zeranol); Progesterone and other progestagens (e.g. allyloestrenol, dydrgesterone, lynoestrenol, norgestrel, norethyndrel, norethisterone, norethisterone acetate, gestodene, levonorgestrel, medroxyprogesterone and megestrol); Antiandrogens (e.g. cyproterone acetate and danazol); Antiestrogens such as tamoxifen and epitiostanol and the aromatase inhibitors, exemestane and 4-hydroxyandrostenedione and its derivatives; Androgens and anabolic agents (e.g. testosterone, methyltestosterone, clostebol acetate, drostanolone, furazabol, nandrolone oxandrolone, stanozolol, trenbolone acetate, dihydro-testosterone, 17-.alpha.-methyl-19-nortestosterone and fluoxymesterone); 5-alpha reductase inhibitors such as finasteride, turosteride, LY-191704 and MK-306; Pituitary hormones and their active derivatives or analogs such as corticotrophin, thyrotropin, follicle stimulating hormone (FSH), luteinising hormone (LH) and gonadotrophin releasing hormone (GnRH); Thyroid hormones (e.g. calcitonin, thyroxine and liothyronine and antithyroid agents such as carbimazole and propylthiouracil); miscellaneous agents such as octreotide; pituitary inhibitors such as bromocriptine; ovulation inducers such as clomiphene; and Hypoglycaemic agents (e.g. insulin, chlorpropamide, glibenclamide, gliclazide, glipizide, tolazamide, tolbutamide, metformin, pioglitazone, rosiglitazone, and troglitazone).

Also contemplated for use herein are steroids, including Corticosteroids (e.g. betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide). Further examples of steroidal antiinflammatory agents for use in the instant compositions include include cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol.

Also contemplated for use herein are Diuretics (e.g. thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and pottasium sparing diuretics, spironolactone, amiloride and triamterene); Antidiuretics (e.g. desmopressin, lypressin and vasopressin including their active derivatives or analogs); Obstetric drugs including agents acting on the uterus such as ergometrine, oxytocin and gemeprost; Prostaglandins such as alprostadil (PGE1), prostacyclin (PGI2), dinoprost (prostaglandin F2-alpha) and misoprostol; Antimicrobials including the cephalosporins such as cephalexin, cefoxytin and cephalothin; Penicillins (e.g. amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, mezlocillin, piperacillin, ticarcillin and azlocillin); Tetracyclines (e.g. minocycline, chlortetracycline, tetracycline, demeclocycline, doxycycline, methacycline and oxytetracycline and other tetracycline-type antibiotics); Aminoglycosides (e.g. amikacin, gentamicin, kanamycin, neomycin, netilmicin and tobramycin); Antifungals (e.g. amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione); Quinolones (e.g. nalidixic acid, cinoxacin, ciprofloxacin, enoxacin and norfloxacin; Sulphonamides (e.g. phthalylsulphthiazole, sulfadoxine, sulphadiazine, sulphamethizole and sulphamethoxazole); Sulphones such as dapsone; Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoylperoxide); Antituberculosis drugs (e.g. ethambutol, isoniazid, pyrazinamide, rifampicin and clofazimine); Antimalarials (e.g. primaquine, pyrimethamine, chloroquine, hydroxychloroquine, quinine, mefloquine and halofantrine); Antiviral agents (e.g. acyclovir and acyclovir prodrugs, famciclovir, zidovudine, didanosine, stavudine, lamivudine, zalcitabine, saquinavir, indinavir, ritonavir, n-docosanol, tromantadine and idoxuridine); Anthelmintics (e.g. mebendazole, thiabendazole, niclosamide, praziquantel, pyrantel embonate and diethylcarbamazine); Cytotoxic agents (e.g. plicamycin, cyclophosphamide, dacarbazine, fluorouracil and its prodrugs, methotrexate, procarbazine, 6-mercaptopurine and mucophenolic acid); Anorectic and weight reducing agents (e.g. dexfenfluramine, fenfluramine, diethylpropion, mazindol and phentermine); Agents used in hypercalcaemia such as calcitriol, dihydrotachysterol and their active derivatives or analogs; Antitussives (e.g. ethylmorphine, dextromethorphan and pholcodine); Expectorants (e.g. acetylcysteine, bromhexine, emetine, guaiphenesin, ipecacuanha and saponins); Decongestants (e.g. phenylephrine, phenylpropanolamine and pseudoephedrine) Bronchospasm relaxants (e.g. ephedrine, fenoterol, orciprenaline, rimiterol, salbutamol, sodium cromoglycate, cromoglycic acid and its prodrugs, terbutaline, ipratropium bromide, salmeterol and theophylline and theophylline derivatives); Antihistamines (e.g. meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine); Local anaesthetics such as lidocaine, benzocaine, tetracaine, chloroprocaine, ropivacaine, bupivacaine, amethocaine, lignocaine, cinchocaine, dibucaine, mepivacaine, prilocaine and etidocaine; Muscle relaxants (e.g. baclofen, diazepam, cyclobenzaprine hydrochloride, dantrolene, methocarbamol, orphenadrine and quinine); Neuromuscular blocking agents (e.g. such as suxamethonium, alcuronium, pancuronium, atracurium, gallamine, tubocurarine and vecuronium).

Also contemplated for use herein are smoking cessation agents such as nicotine, bupropion and ibogaine; allergens for desensitisation such as house dust mite allergen; nutritional agents, such as vitamins, essential amino acids and essential fats; keratolytics such as the alpha-hydroxy acids, glycollic acid and salicylic acid; anti-acne agents such as isotretinoin, tretinoin and benzoyl peroxide; anti-psoriasis agents such as etretinate, cyclosporin and calcipotriol; anti-itch agents such as capsaicin and its derivatives such as nonivamide; and anticholinergic agents, which are effective for the inhibition of axillary sweating and for the control of prickly heat (e.g. methatropine nitrate, propantheline bromide, scopolamine, methscopolamine bromide, and antiperspirants (quaternary acyloxymethyl ammonium salts).

It is to be understood that the above list of ingredients is for purposes of illustration and is not provided as an all-inclusive list of all the drugs which may be beneficially formulated or reformulated using the compositions of the present invention.

Methods of Use

According to other embodiments of the present invention, methods of using topical compositions for the treatment of skin are provided. Some conditions that may be treated by these compositions and methods include acne, actinic damage, dandruff, eczema, fine lines, psoriasis, warts, inflammation, infection, and wrinkles. The composition may be applied from about twice a week to about four times a day. In another embodiment, the composition is applied from about once every other day to about three times a day. In yet another embodiment, the composition is applied from about once daily to about twice daily.

Once desirable effects are achieved, the frequency and dosage can be reduced to a maintenance level. The maintenance level will vary according to the individual, but in one embodiment is from about 1/10 to about 1/2 of the previous dose and/or frequency. In another embodiment, the maintenance level is from about 1/5 to about 1/3 of the previous dose and/or frequency. The dosages and frequencies listed here are guidelines only and can be modified based on a variety of different factors including the condition of the skin to be treated, the topical or systemic administration of other compounds that might affect the skin, and other systemic conditions such as kidney or liver conditions, that might affect the metabolism of the administered compounds.

In some cases, particularly in elderly people, these conditions are accompanied by irregularities in pigmentation. Accordingly, certain embodiments of the present invention include skin lighteners for treating such irregular coloration. To treat one of these conditions, an effective amount of a topical composition comprising one or more of the above ingredients is applied to the skin in need of treatment.

According to some embodiments of the present invention, compositions and methods are provided for treatment of wrinkles with toxin compounds for chemical denervation without the need for injection or other invasive penetration. In one embodiment, for example, a topical formulation for the treatment of wrinkles caused by muscular contraction comprises an amphipol polymer ionically paired with a chemodenervation agent, together with at least one TJ-modulating peptide in a dermatologically acceptable vehicle. The chemodenervation agent may be any agent capable of temporally denervating or rendering powerless a target muscle. For example, the chemical denervation agent may be a botulinum toxin (e.g. BOTOX®), an α-neurotoxin, a conotoxin, or the like.

The inventive compositions and methods provide new ways to administer a chemodenervation agent, such as a botulinum toxin, α-neurotoxin, conotoxin, and the like, with increased efficiency and without the pain and discomfort normally associated with penetrating injections. Besides pain and discomfort, injections may cause localized swelling or edema, capillary hemorrhage and inflammation, which are generally avoided when the inventive compositions are used.

Methods of Preparation

The inventive topical compositions described herein may be made by any suitable method, including standard methods used to make cosmetic preparations and pharmaceutical compositions intended for application on the skin. Non-limiting examples of suitable procedures include mixing techniques (both manual and mechanical mixing), homogenization mixing and sweep mixing. The mixing techniques can be chosen based on variables such as the viscosity of the components to be mixed and the volume of those components, as well as the relative proportion of lipid-soluble and water-soluble ingredients. The amphipol polymer and charged bioactive agent can be ionically-paired and then mixed with the remaining ingredients in the delivery vehicle, as exemplified herein. A subject of the invention is thus also a process for preparing the compositions as described herein.

Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

All patents and patent publications referred to herein are hereby incorporated by reference in their entirety.

The following examples are included to demonstrate certain preferred embodiments of the invention. It will be appreciated by those of skill in the art that the techniques disclosed in the examples which follow represent techniques discovered by the inventor to function well in the practice of the invention, and thus can be considered to constitute preferred modes for its practice. However, those of skill in the art will appreciate that many changes can be made without departing from the spirit and scope of the invention.

EXAMPLES

Example 1: Formulation of Stable Protein Microemulsions

Microemulsions were set up as "water-in-oil" emulsions starting with the preparation of a combined oil/surfactant phase first. Each component was added by weight on a scale. The relative ratios of each component are expressed as % weight of the total weight of the complete emulsion. The correctly formulated microemulsion constitutes a homogenous, optically clear and transparent liquid formed by mixing 3 principle constituents:

1) Oil phase
2) Surfactant/Co-surfactant phase, containing amphipol polymer A8-35
3) Aqueous phase, containing an a neurotoxin (MCPT-201), buffer and, optionally, the TJ-modulating peptide.

In the formulation process, for the purpose of added flexibility in regard to the target concentration of active protein, the oil (1) and surfactant/co-surfactant phases (2) are combined into one aliphatic phase that can be prepared in bulk quantities ahead of time and stored separately. This aliphatic component (1+2) can then be "charged" (mixed) at a later time with the aqueous phases containing varying amounts of the water-soluble active protein Alternatively, the aliphatic component can also be charged with varying amounts (30-35% weight) of the aqueous phase to modulate the viscosity/fluidity of the microemulsion. The microemulsion's viscosity/fluidity is directly proportional to the amount (% weight) of the aqueous phase. The aliphatic microemulsion constituent (1+2) is a homogenous liquid that can be stored either frozen (as solidified wax), or at 4° C.-12° C. and RT for at least 6 months, probably much longer with the addition of fat-soluble antioxidants. The aqueous phase containing the active protein drug can thus be stored separately under conditions best for the protein, or prepared freshly from a concentrated protein stock just before mixing the finished microemulsion.

Mixing of the aliphatic component and the aqueous phase does not require excessive kinetic energy. It is done simply by hand-flipping the tube (5 minutes) or on a vortexer at maximum speed for two minutes. The aqueous and lipophilic components of the microemulsion do not separate after mixing even when centrifuged for 10 minutes at 8000 rpm). The microemulsion can likely withstand even higher centrifugal forces before it starts to separate.

TABLE 1

| Phase | Component | % Weight | Supplier | Cat# |
|---|---|---|---|---|
| Oil Phase 15% w/w | Isopropyl myristate (98% purity) | 5.25 | Sigma | 172472-1L |
| | Oleic acid (99% purity) | 9.75 | Sigma | O1008-5G |
| Co-Surfactant Phase (15% w/w) | Isopropyl alcohol (99% purity) | 11 | Sigma | I9516-500ML |
| | Propylene glycol (99.5% purity) | 3.75 | Sigma-Aldrich | W294004-1KG-K |
| | R-(+)-Limonene (97% purity) | 0.3% | Sigma | 183164-5ML |
| Surfactant Phase (38% w/w) | Tween 80 (BioXtra) | 37.15% | Sigma | P8074-500ML |
| | Amphipol A8-35 (AP) | Variable* | Anatrace | |
| | DMPG (Phospholipid) | 0.1-0.5% | Affimetrix (Anatrace) | D514 1 GM |
| Buffer/Protein Phase 32% w/w | MCPT-201 | variable conc.* 3-20 mg/ml | N/A | N/A |
| | Transdermal Peptide) | variable conc.* 6-30 mg/ml | AnaSpec | 62066 |

*The amount of amphipol polymer is determined by the amount of active protein in the microemulsion. The molarity ratio between the amphipol and the protein in the microemulsion should be between about 1:1 and 2:1. The optimal molar ratio for each bioactive compound depends on its molecular weight and needs to be determined empirically within the range of 1:1 and 10:1.

*The TJ peptide concentration needs to be adjusted to provide a 5-10 fold molar excess of TDP over MCPT-201. For other bioactive compounds the best concentration/amount of TJ peptide in the formulation needs to be empirically determined in the range of 2 to 20 fold molar excess.

TABLE 2

| Phase | Component | % Weight | Supplier | Cat# |
|---|---|---|---|---|
| Oil Phase 15% w/w | Isopropyl myristate (98% purity) | 8.25 | Sigma | 172472-1L |
| | Oleic acid (99% purity) | 6.75 | Sigma | O1008-5G |
| Co-Surfactant Phase (15% w/w) | Isopropyl alcohol (99% purity) | 11 | Sigma | I9516-500ML |
| | Propylene glycol (99.5% purity) | 3.75 | Sigma-Aldrich | W294004-1KG-K |
| | R-(+)-Limonene (97% purity) | 0.3% | Sigma | 183164-5ML |

TABLE 2-continued

| Phase | Component | % Weight | Supplier | Cat# |
|---|---|---|---|---|
| Surfactant Phase (38% w/w) | Tween 80 (BioXtra) | 37.15% | Sigma | P8074-500ML |
| | Span 80 | 3.42% | Sigma | S6760-250ML |
| | Amphipol A8-35 (AP) | Variable* | | |
| | DMPG (Phospholipid) | 0.1-0.5% | Affimetrix (Anatrace) | D514 1 GM |
| Buffer/Protein Phase 32% w/w | MCPT-201 | variable conc.* 3-20 mg/ml | N/A | N/A |
| | TDP (Transdermal Peptide) | variable conc.* 6-30 mg/ml | AnaSpec | 62066 |

Formulation Design Rules and Dependencies

For improved stability both formulations are designed to match the HLB (hydrophilic-lipophilic balance index) of the oil phase with the HLB of the surfactant phase. In the first formulation a 65%/35% oleic acid/isopropyl myristate (HLB 15.075) mixture matches the HLB 15 of Tween 80. In the second formulation a 45%/55% oleic acid/isopropyl myristate mixture with an HLB of 13.98 matches the HLB 14 of a 91%/9% surfactant mixture of Tween 80/Span 80.

The absolute amount of isopropyl alcohol or equivalent co-solvents (pentanol, 1,2-pentadiol, 1,5 pentadiol) is critical as is the ratio between isopropanol and propylene glycol for the stability and fluidity of the microemulsion. Reduction of isopropanol <11% w/w increases the viscosity of the aliphatic phase. Further reduction <10% w/w turns the combined oil/surfactant/cosurfactant phase gradually into a semi-solid wax at ambient temperature. The same effect results from an increase of the propylene glycol amount relative to the amount of isopropanol, while keeping the combined amount (15%) of both co-solvents unchanged.

The aqueous phase is preferably set up with a buffer optimal for the long-term stability of the active protein. In the preliminary Franz cell studies a 50 mM MES-KOH, 20 mM NaCl, 0.1 mM EDTA, 0.5 mM oxidized glutathione (GSSG) at pH 6.0 was used as the aqueous phase. Alternative aqueous buffers should be adjusted to the same pH and have maximum buffer capacity within +/−0.2 pH units. The oxidized GSSG is added for preventing reduction and re-shuffling of critical disulfide bonds in the MCPT-201 protein.

Example 2: Franz Diffusion Cell Studies

The purpose of these studies was to demonstrate proof of principle for transcutaneous passage of the positively charged MCPT-201 protein by way of a microemulsion carrier formulated with the subject skin penetration enhancers. Three principle skin penetration enhancers were compared assessing the transdermal flux of MCPT-201 in Franz cells mounted with porcine skin. The collected filtrate from these samples was then assayed for neuromuscular activity on isolated innervated murine diaphragm muscle.

Materials and Methods

Franz Cells for In Vitro Transdermal Flux Studies

Franz cells are glass devices comprising an upper chamber for the donor solution and a lower receiving chamber clamped together between which a diffusion barrier (skin tissue) is mounted. The skin diffusion barrier double serves as a sealing gasket between the upper and lower glass chambers. The receiving chamber is filled with buffer and contains a magnetic stir bar. The donor chamber on top of the skin tissue is filled with the protein-containing microemulsion serving as the donor solution. In a typical experiment of the study, Franz cells loaded with microemulsion and receiving buffer were incubated at 37° C. in an incubator under continuous mixing over a time course of 8 to 24 hours.

To prevent microbial growth proteolytic degradation in the receiving chamber the buffer was supplemented with the antibiotics carbenicillin (100 ug/ml), kanamycin (20 ug/ml) and chloramphenicol (30 ug/ml) and with a cocktail of proteinase inhibitors.

Franz cells used in this study were adapted for protein transdermal flux experiments by reducing the volume of the receiving chamber to 3 to 5 ml to minimize sample dilution. The fill volume of the donor chamber was limited 1 ml. The orifice of these "miniature" Franz cells through which the protein exchange between the upper and lower chambers takes place was set to 0.5-0.64 $cm^2$.

Protein Sample Processing

In the absence of a sensitive and reliable detection assay for the MCPT-201 protein and the native alpha cobratoxin the presence of the analyte in the receiving chamber buffer was analyzed by PAGE SDS gel electrophoresis using appropriate polypeptide size markers and venom-purified alpha cobratoxin as quantitative and qualitative marker protein. The samples from the Franz cells receiving chambers were too dilute for direct gel analysis and had to be concentrated first. For the first study this was done in a two-step process. After completion of the Franz cell incubation the receiving chamber samples were collected and passed through a 0.22 um PES syringe filter (Whatman) to sterilize the solution and remove insoluble matter. Then the proteins and polypeptides in the 5 and 3 ml receiving buffer samples (in 25 mM Citrate-Phosphate buffer, pH 6.0) were fractionated by ultrafiltration through a membrane with a 50 kDa MWCO pore size first (Millipore UFC905008 Regenerated Cellulose Amicon Ultra Centrifugal Filter Unit). The filtrate of the first ultrafiltration step was concentrated down to 50 ul by ultrafiltration though spin columns (Pall Nanosep; Sigma cat #OD003C33) with a 3000 Da MWCO pore size membrane at 13K rpm for 20 to 3-0 minutes.

Approximately ⅓ of the total concentrated sample volume (15 ul) was analyzed on a 4-20% PA gradient gel in Tis-Tricine buffer running buffer (BioRad; Criterion Peptide Gel 345-0064). After electrophoretic separation (appr. 1 hour at 110 V; BioRad Criterion Cell) the gels were fixated in 40% methanol/10% acetic acid and stained with SYPRO Ruby (BioRad; SYPRO Ruby Protein Gel Stain #170-3126) or Coomassie Blue. Gel staining was performed according to the manufacture's protocol overnight.

For the second study this procedure was modified to include a chromatographic enrichment/purification step over a HiTrap SP-Sepharose cation exchange column (GE Healthcare). Both MCPT-201 and alpha cobratoxin are highly positively charged proteins with a pI of 8.2. They are routinely purified on cation exchange resigns such as SP-Sepharose. The sample buffer in the Franz cell receiving chamber was changed to 50 mM MES-NaOH, 20 mM NaCl, 0.1 mM EDTA, pH 6.0 in order to make samples directly compatible with cation exchange chromatography over SP-Sepharose.

This sample buffer is the same buffer used to equilibrate the column and load the MCPT-201 protein on SP-Sepharose columns for purification. After finishing the incubation of the Franz cells, the receiving chamber samples were sterilized by filtration through a 0.22 um PES syringe filter. Further, all samples were adjusted to 8 ml volume with the 50 mM MES-NaOH buffer and loaded onto a 1 ml HiTrap SP-Sepharose column (GE) at low the flow rate of 0.5 ml/min. Prior to sample loading the columns were equilibrated with 5 CVs of the same buffer. The sample-loaded columns were washed with 5 CVs of the loading (sample) buffer. The positively charged protein fraction was eluted in MES-NaOH, 300 mM NaCl, 0.1 mM EDTA, pH 6.0. The SP-Sepharose protein eluate was pooled and sterile filtered through a 0.22 um PES syringe filter and concentrated down to 50 ul as previously described. SDS PAGE analysis with the chromatography-purified protein samples was carried out as previously described.

Skin Tissue for Franz Cell Studies

For all experiments, fresh never frozen porcine skin specimens were shipped on dry ice from PEL-Freeze Inc. (2-1.5 $cm^2 \times 2$ mm size) and used within 24 hours of receipt.

Calculation of the Transdermal Flux Rate

The amount of specific protein (MCPT-201 and alpha cobratoxin) delivered transdermally to the receiving buffer filtrate was determined semi-quantitatively by comparative SDS PAGE analysis. Polypeptide size markers and samples of a serial dilution of alpha-cobratoxin with known concentrations (25 ng to 2 ug) co-migrated on each gel to allow the identification of the correct protein band by size and the quantification of the specific protein band. The transdermal flux rate was calculated by the formula:

$$\frac{M}{T \times A}$$

"M" is the total amount of specific protein in ug detected in the buffer of the receiving chamber "T" is the incubation time in hours and "A" is the skin area (Franz cell orifice) in $cm^2$ This approach to determine the transdermal flux rate represents an end point analysis. The limited sensitivity of the detection method did not allow for measuring the kinetics of the transdermal protein flux by analyzing samples taken at various time points during the incubation. Therefore the flux rate may be artificially lowered if most of the transfer takes place in the first hours of the experiment, when the skin tissue is still "fresh."

DMSO-Containing Microemulsions

Published studies on transdermal delivery of proteins in microemulsion carriers reported the use of DMSO as an effective chemical skin penetration enhancer. Despite the well-known and significant drawbacks associated with human use, the efficacy of DMSO as a chemical skin penetration enhancer provides an appropriate comparison since it is considered a gold standard for promoting the skin penetration of small molecule drugs.

Results and Discussion

Comparison of Skin Penetration Enhancer Combinations

The goal of the first study was to determine whether microemulsions formulated with various chemical skin penetration enhancers could facilitate the transdermal passage of MCPT-201. Three different microemulsions were formulated all with a final MCPT-201 concentration of 0.6 mg/ml emulsion. The base formulation of the three microemulsions was the same as described above. They differed by the presence or absence of the following biochemical skin penetration enhancer combinations.

E8WPT-1 containing 0.6 mg/ml MCPT-201; TJ-modulating peptide plus phospholipids (DMPC)

E8WPT-2 containing 0.6 mg/ml MCPT-201; amphipol polymer plus phospholipids (DMPC)

E8WPT-3 containing 0.6 mg/ml MCPT-201; amphipol polymer only

MCPT-201 could be detected in the receiving chamber buffer of all three samples. The respective transdermal flux rates were 0.037 μg/hour per $cm^2$ for E8WPT-1, 0.195 μg/hour per $cm^2$ for E8WPT-2 and 0.117 μg/hour per $cm^2$ for E8WTP-3. The total yield of transdermally delivered MCPT-201 after 8 hours of incubation were estimated at 200 ng for E8WTP-1, 1 μg for E8WTP-2 and 0.6 μg for E8WTP-3, respectively. The results of the first study are shown in FIG. 1 and summarized in Table 3 below.

TABLE 3

| Microemulsions | MCPT-201 Transdermal Flux Rate in μg/hour per $cm^2$ | Amount of MCPT-201 in Receiving Buffer after 8 h in μg | Transdermal Efficiency % delivered from loaded amount |
|---|---|---|---|
| E8WPT-1 | 0.037 | 0.2 | 0.02 |
| E8WPT-2 | 0.195 | 1.0 | 0.1 |
| E8WTP-3 | 0.117 | 0.6 | 0.06 |

Comparison Against DMSO as Positive Control

In the second study, the DMSO-containing microemulsion was compared against a microemulsion formulated with the amphipol polymer and TJ-modulating, and a negative control microemulsion without these additional skin penetration enhancers. The following three microemulsion formulations were tested:

ME11a 2 mg/ml MCPT-201, 4 mg/ml TJ-modulating peptide; 2 mg/ml Amphipol A8-35

ME11a-NC ME11a without MCPT-201 protein (negative control)

ME9a 2 mg/ml MCPT-201; 5% DMSO replacing propylene glycol

Figure 2:
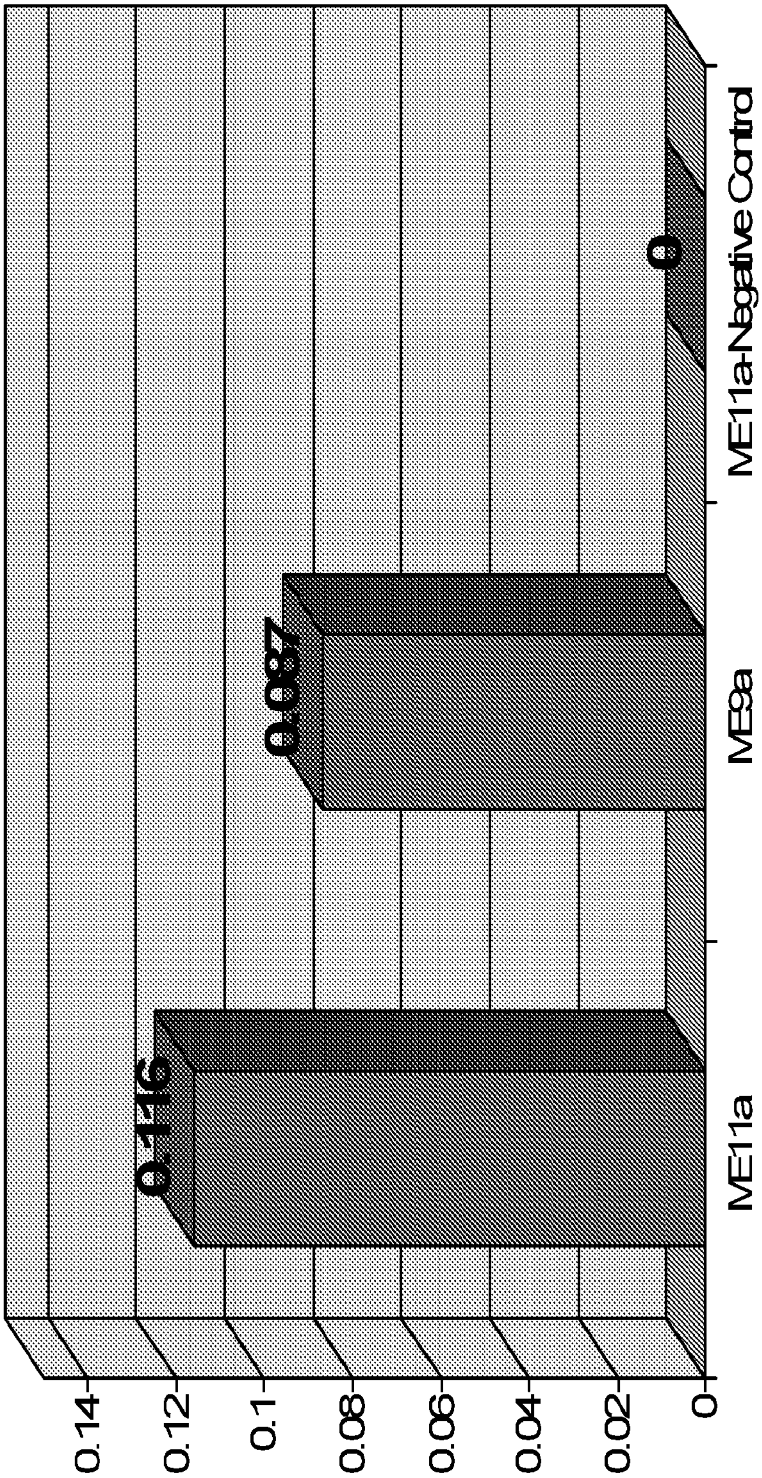
FIG. 2 is a graph comparing the transdermal flux rates of a preferred embodiment of the subject formulation with 5% DMSO and control as measured in a Franz diffusion cell assay.

The samples from the Franz cell receiving chambers were analyzed as indicated above using SDS-PAGE for quantification, and the results are shown in FIG. 2 and summarized in Table 4 below

TABLE 4

| Microemulsions | MCPT-201 Transdermal Flux Rate in μg/hour per $cm^2$ | Amount of MCPT-201 in Receiving Buffer after 11 hours in μg | Transdermal Efficiency % delivered from loaded amount |
|---|---|---|---|
| ME11a | 0.116 | 2 | 0.1 |
| ME9a | 0.087 | 1.5 | 0.075 |
| ME11a-NC | 0.0 | 0.0 | 0.0 |

Example 3: Bioactivity Assay

The bioactivity of the receiving chamber fraction from each of the above samples was determined in an in vitro mouse diaphragm assay. Three samples were assayed as follows: 1) DMSO-treated toxin (corresponding to ME9a fraction), 2) non-DMSO toxin (corresponding to ME11a fraction) and 3) negative control (corresponding to ME11a-NC fraction). All were tested with the mouse diaphragm neuromuscular junction.

Figure 3:
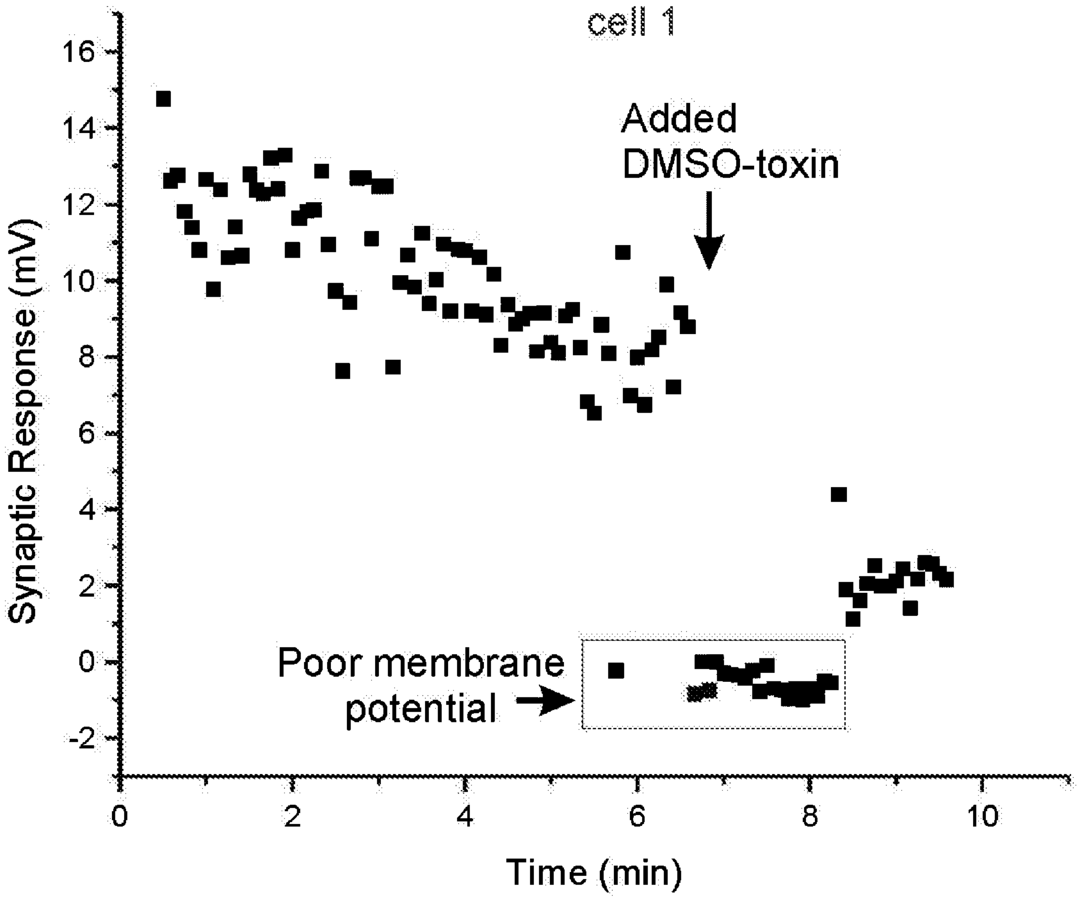
FIG. 3 shows the relative bioactivity of concentrated protein fractions from the receiving chamber of the DMSO-based formulation on isolated innervated mouse diaphragm.
Figure 4:
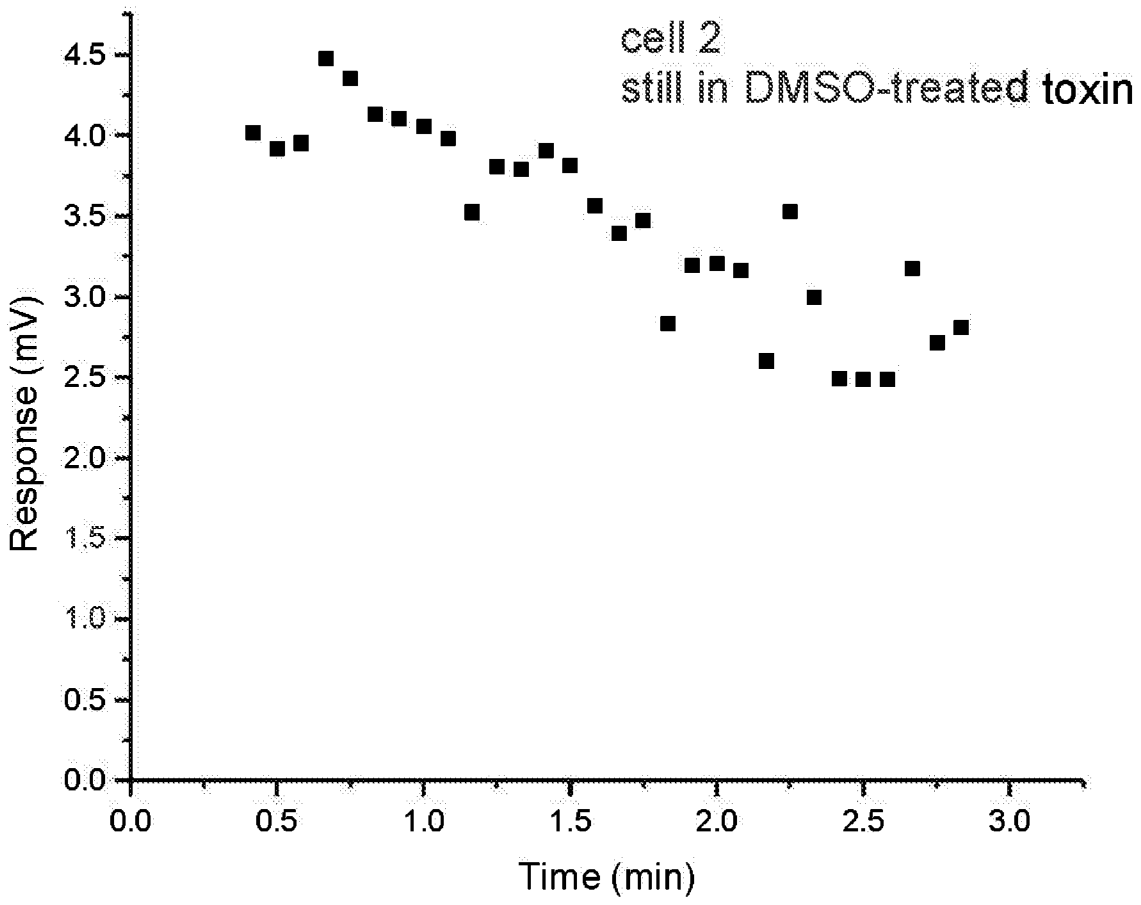
FIG. 4 shows the relative bioactivity of concentrated protein fractions from the receiving chamber of the DMSO-based formulation on isolated innervated mouse diaphragm.
Figure 5:
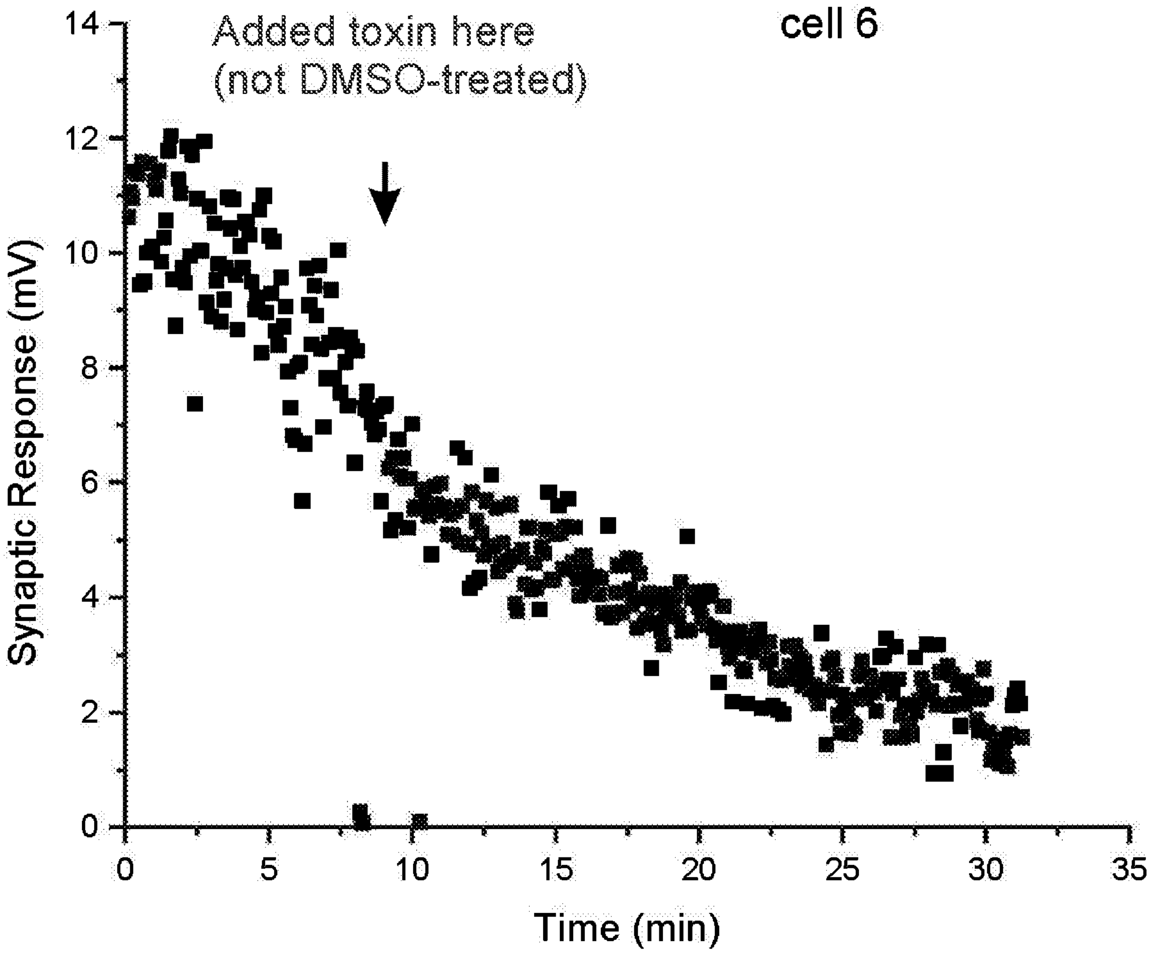
FIG. 5 shows the relative bioactivity of concentrated protein fractions from the receiving chamber of the inventive formulation on isolated innervated mouse diaphragm.
Figure 6:
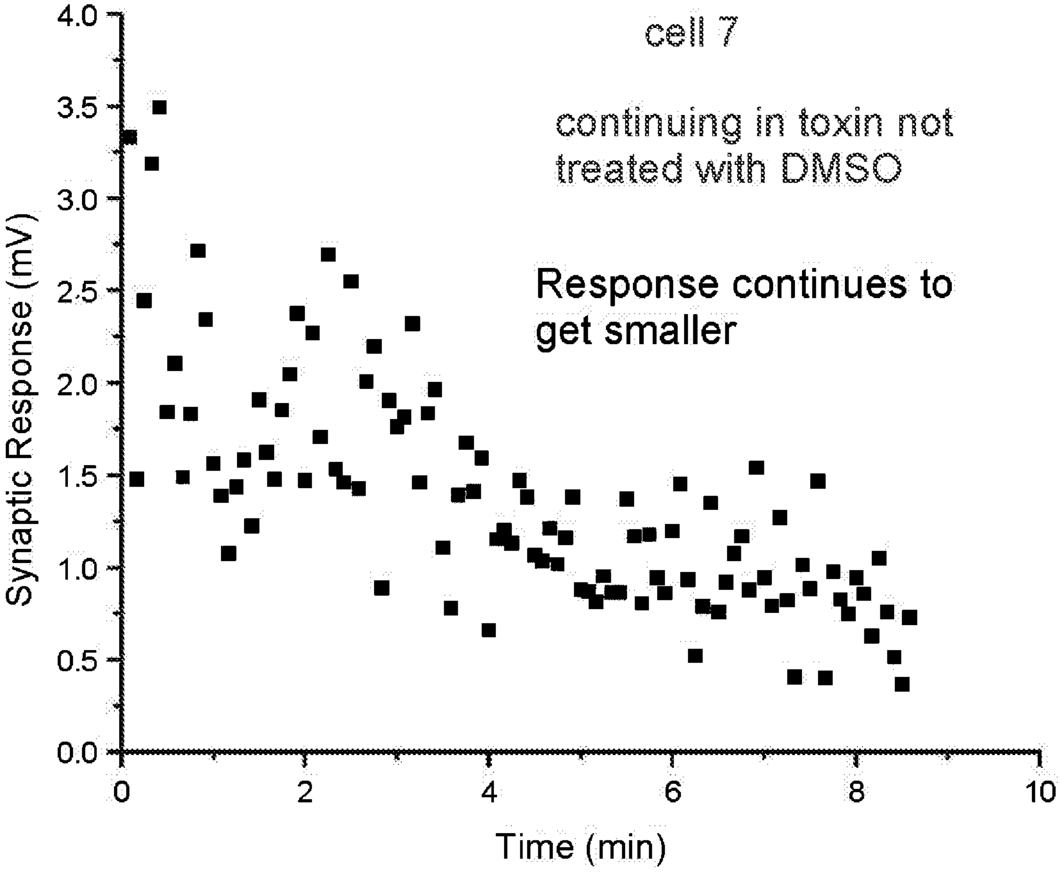
FIG. 6 shows the relative bioactivity of concentrated protein fractions from the receiving chamber of the inventive formulation on isolated innervated mouse diaphragm.

Specifically, 60 ul of the DMSO-treated toxin was added to the diaphragm in 2 ml of saline. (FIGS. 3 & 4) Four more cells were recorded for another 20 minutes after cell 2 and there was still a moderate response. The non-DMSO toxin (50 ul in 2 ml) was then added to cell 6 (FIG. 5). The synaptic response continued to get smaller over the next hour. Four more cells were tested after cell 7. (FIG. 6). The negative control was tested on a separate diaphragm and recorded from 5 cells. As expected, the synaptic response remained strong for over an hour with the negative control.

The relative bioactivity of the concentrated protein fractions from the Franz cell receiving chambers on isolated innervated mouse diaphragm muscle follows below in Table 5, in comparison with direct application of stock MCPT-201.

TABLE 5

| Microemulsions | Max. Inhibition of Resting Action Potential in % | Time of Onset to Maximum Inhibition | Δ RAP per minute |
|---|---|---|---|
| ME11a | 50% after 10 min. 72% after 20 min. >90% after 1 h | 30-60 min. | −0.5 mV/min |
| ME9a | <50% (after 20 min.) | >60 min. | −0.33 mV/min |
| ME11a-NC | No effect | N/A | N/A |
| 2 μmol MCPT-201 | >95% | 7 min | −1.5 mV/min |

Conclusions

Isopropyl myristate, oleic acid, limonene and propylene glycol have been identified as skin penetration enhancers in past transdermal delivery studies with small molecule drugs. Little effect was seen in regard to enhancing skin penetration of the positively charged protein MCPT-201, since no protein could be detected in the receiving buffer fraction from the Franz cell experiments when the amphipol polymer and/or TJ-modulating peptide were omitted from the formulation of the microemulsion. These studies clearly demonstrate the most effective transdermal delivery of a large (~7 kD) hydrophilic protein was when complexed with amphipol polymer and combined with TJ-modulating peptides according to the subject invention.

An optimal microemulsion formulation including both the Amphipol polymer and the TJ-modulating peptide was compared against a microemulsion including DMSO as a positive control. Comparable transdermal flux rates were obtained with both formulations as shown in FIG. 2. Notably however the DMSO appears to have an adverse impact on protein activity, as the time to onset in the diaphragm inhibition assays was longer and maximal inhibition was lower for the DMSO fraction as compared to the non-DMSO fraction. The non-DMSO fraction compares favorably to stock MCPT-201, demonstrating that the inventive formulation delivered MCPT-201 in active form and in cosmetically effective amounts.

Example 4: Comparison Neurotoxin Assay

Waglerin-1 (Wtx-1) is a peptide originally isolated from the venom of the Wagler's pit viper (*Trimeresurus wagleri*). Utkin Y. N. et al. Azemiopsin from Azemiops *feae* Viper Venom, a Novel Polypeptide Ligand of Nicotinic Acetylcholine Receptor. *J. Biol. Chem.* 2012, August 3; 287(32): 27079-86. This 22 amino-acid peptide is a competitive antagonist of muscle nicotinic acetylcholine receptors and competes with α-bungarotoxin. This assay compares the transdermal delivery of both of these molecules.

Bioactive, synthetic, full-size Waglerin-1 and α-bungarotoxin are obtained from commercials sources with a FITC-label for the transdermal experiments. The assay is conducted in accordance with Examples 1-3 above with human cadaveric skin tissue replacing the porcine skin employed in the earlier assays. The receiving chamber fraction is collected and analyzed for fluorescence, and follow-up HPLC and/or mass spectrometry studies are done to quantify and confirm the identify of the transferred protein(s).

Example 5: Transdermal Insulin Delivery

Insulin has a negative net charge and is ionically paired with a PMAL amphipol polymer in accordance with the subject invention. Recombinant, human insulin is obtained from a commercial source with a FITC-label (Sigma-Aldrich cat #I3661-5MG) and the Franz diffusion cell assays are run in accordance with the foregoing examples. The receiving chamber fraction is collected and analyzed using a commercial quantitative fluorescent ELISA kit for the detection of human insulin (Millipore).

Certain modifications and improvements will occur to those skilled in the art upon a reading of the foregoing description. It should be understood that not all such modifications and improvements have been included herein for the sake of conciseness and readability, but are properly within the scope of the following claims.

The invention claimed is:

1. A topical formulation for dermal delivery comprising an amphipol polymer ionically paired with at least one charged bioactive agent in a dermatologically acceptable vehicle, wherein said dermatologically acceptable vehicle is a water-in-oil or oil-in-water nanoemulsion, and said at least one charged bioactive agent is a selected from the group consisting of neurotoxins, antibodies and insulin, and said amphipol polymer is selected from the group consisting of A8-35 and PMAL.

2. The topical formulation according to claim 1, further comprising a moisturizing agent a humectant, a surfactant, a silicone-containing compound, a UV agent, a chelating agent, an essential oil, a skin lightener, a preservative, a thickening agent, a structuring agent, vitamin, a cosmetic ingredient, a pharmaceutical ingredient, or an antioxidant.

3. The topical formulation according to claim 1, wherein said dermatologically acceptable vehicle is a water-in-oil nanoemulsion and the amphipol polymer/at least one charged bioactive agent complex partitions to the oil phase of the nanoemulsion.

4. A method for improving skin appearance in a subject in need thereof comprising applying to the skin of the subject the topical formulation according to claim 1.

5. A topical formulation for dermal or transdermal delivery comprising an amphipol polymer ionically paired with at least one charged bioactive agent, together with at least one TJ-modulating peptide in a dermatologically acceptable vehicle, wherein said dermatologically acceptable vehicle is a water-in-oil or oil-in-water nanoemulsion, and wherein said at least one charged bioactive agent is selected from the group consisting of neurotoxins, antibodies and insulin or peptide and said amphipol polymer is selected from the group consisting of A8-35 and PMAL.

6. The topical formulation according to claim 5, wherein said at least one TJ-modulating peptide is selected from the group consisting of NH2-ACSSSPSKHCG-COOH, synthetic biomimetic peptide analogues of occludin's first and second extracellular loops, and synthetic biomimetic peptide analogues of claudin-actin peptides.

7. The topical formulation according to claim 5, wherein said dermatologically acceptable vehicle is a water-in-oil nanoemulsion and the amphipol polymer/at least one charged bioactive agent complex partitions to the oil phase of the nanoemulsion, and wherein the at least one TJ-modulating peptide partitions to the aqueous phase of the nanoemulsion.

8. A method of improving an appearance of fine lines and wrinkles in a subject in need thereof, comprising topically applying an effective amount of an anti-wrinkle composition comprising an amphipol polymer ionically paired with a chemodenervation agent, together with a at least one TJ-modulating peptide in a dermatologically acceptable vehicle to a skin of the subject so as to lessen and improve the appearance of fine lines and wrinkles, wherein said dermatologically acceptable vehicle is a water-in-oil or oil-in-water nanoemulsion and said amphipol polymer is selected from the group consisting of A8-35 and PMAL.

9. The method according to claim 8, wherein said dermatologically acceptable vehicle is a water-in-oil nanoemulsion and the amphipol polymer/chemodenervation agent complex partitions to the oil phase of the nanoemulsion, and the at least one TJ-modulating peptide partitions to the aqueous phase of the nanoemulsion.

10. A method for treating a skin disorder in a subject in need thereof comprising applying to a skin of the subject a therapeutically effective amount of a therapeutic composition comprising an amphipol polymer ionically paired with at least one charged bioactive agent in a dermatologically acceptable vehicle, wherein said dermatologically acceptable vehicle is a water-in-oil or oil-in-water nanoemulsion, said at least one charged bioactive agent is selected from the group consisting of neurotoxins, antibodies and insulin, and said amphipol polymer is selected from the group consisting of A8-35 and PMAL, and optionally further comprising at least one TJ-modulating peptide for transdermal delivery, so as to treat the skin disorder of the subject.

11. The method according to claim 10, wherein said dermatologically acceptable vehicle is a water-in-oil nanoemulsion and the amphipol polymer/at least one charged bioactive agent complex partitions to the oil phase of the nanoemulsion, and wherein the at least one TJ-modulating peptide partitions to the aqueous phase of the nanoemulsion.

12. The method according to claim 10, wherein said at least one TJ-modulating peptide is selected from the group consisting of NH2-ACSSSPSKHCG-COOH, synthetic biomimetic peptide analogues of occludin's first and second extracellular loops, and synthetic biomimetic peptide analogues of claudin-actin peptides.

13. A method of enhancing penetration of a skin by at least one charged biologically active protein or peptide comprising applying to the skin of a subject in need thereof a composition comprising an amphipol polymer ionically paired with at least one charged biologically active protein or peptide in a dermatologically acceptable vehicle, wherein said dermatologically acceptable vehicle is a water-in-oil or oil-in-water nanoemulsion, wherein said amphipol polymer is selected from the group consisting of A8-35 and PMAL, wherein said at least one charged biologically active protein or peptide is selected from the group consisting of neurotoxins, antibodies and insulin, wherein the composition optionally further comprises at least one TJ-modulating peptide for transdermal delivery, and wherein the penetration of the at least one charged biologically active protein or peptide is increased with respect to the penetration of the same agent without the amphipol polymer.

14. The method according to claim 13, wherein said dermatologically acceptable vehicle is a water-in-oil nanoemulsion and the amphipol polymer/at least one charged biologically active protein or peptide complex partitions to the oil phase of the nanoemulsion, and wherein the at least one TJ-modulating peptide partitions to the aqueous phase of the nanoemulsion.

15. The method according to claim 13, wherein said at least one TJ-modulating peptide is selected from the group consisting of NH2-ACSSSPSKHCG-COOH, synthetic biomimetic peptide analogues of occludin's first and second extracellular loops, and synthetic biomimetic peptide analogues of claudin-actin peptides.

* * * * *